US012629351B2

(12) United States Patent
Chandrasekhar et al.

(10) Patent No.: US 12,629,351 B2
(45) Date of Patent: May 19, 2026

(54) HDAC INHIBITORS FOR IDIOPATHIC PULMONARY FIBROSIS AND OTHER LUNG INFLAMMATORY DISORDERS

(71) Applicant: COUNCIL OF SCIENTIFIC AND INDUSTRIAL RESEARCH (AN INDIAN REGISTERED BODY INCORPORATED UNDER THE REGN, OF SOC. ACT (ACT XXI OF 1860)), New Delhi (IN)

(72) Inventors: Srivari Chandrasekhar, Telangana (IN); Prathama S Mainkar, Telangana (IN); Chada Raji Reddy, Telangana (IN); Sistla Ramakrishna, Telangana (IN); Andugulapati Sai Balagi, Telangana (IN); Kuncha Madhusudana, Telangana (IN); Muppidi Mohan Venkata Subbarao, Telangana (IN); Tirunavalli Satya Krishna, Telangana (IN)

(73) Assignee: COUNCIL OF SCIENTIFIC AND INDUSTRIAL RESEARCH (AN INDIAN REGISTERED BODY INCORPORATED UNDER THE REGN. OF SOC. ACT (ACT XXI OF 1860)), New Delhi (IN)

( * ) Notice: Subject to any disclaimer, the term of this patent is extended or adjusted under 35 U.S.C. 154(b) by 508 days.

(21) Appl. No.: 18/044,024

(22) PCT Filed: Sep. 3, 2021

(86) PCT No.: PCT/IN2021/050851
§ 371 (c)(1),
(2) Date: Mar. 3, 2023

(87) PCT Pub. No.: WO2022/049599
PCT Pub. Date: Mar. 10, 2022

(65) Prior Publication Data
US 2023/0321038 A1     Oct. 12, 2023

(30) Foreign Application Priority Data
Sep. 5, 2020     (IN) .............................. 202011038497

(51) Int. Cl.
*A61K 31/404*     (2006.01)
*A61K 31/4439*     (2006.01)
*A61P 11/00*     (2006.01)

(52) U.S. Cl.
CPC ........ *A61K 31/404* (2013.01); *A61K 31/4439* (2013.01); *A61P 11/00* (2018.01)

(58) Field of Classification Search
CPC ... A61K 31/404; A61K 31/4439; A61P 11/00; A61P 1/16; A61P 9/00; A61P 13/12
See application file for complete search history.

(56) References Cited

U.S. PATENT DOCUMENTS 7,368,572 B2     5/2008   Sendzik

FOREIGN PATENT DOCUMENTS

WO     WO 2008068170         6/2008
WO     WO 2019102488 A1     5/2019

OTHER PUBLICATIONS

Lyu et al., Ther Adv Chronic Dis, Jan. 2019, vol. 10: 1-19 (Year: 2019).*

(Continued)

*Primary Examiner* — San Ming R Hui
(74) *Attorney, Agent, or Firm* — Fish & Richardson P.C.

(57)     ABSTRACT

The present invention relates to compound of Formula 1 for use in treating IPF, by reducing collagen deposition in lungs, attenuating the fibrotic marker's expression (in IPF cell-lines Bleomycin induced rat lungs) and improving the bleomycin (Continued)

(1A)

(1B)

(1C)

induced pathological changes in rat lungs, and ARDS, by reducing the cytokine storm. The invention also relates to compound of Formula 1 for use in treating various fibrotic disorders like lung injuries caused by virus or bacterial infections, cardiac, hepatic and kidney fibrosis.

12 Claims, 18 Drawing Sheets

(56) References Cited

OTHER PUBLICATIONS

Belikov, "Pharmaceutical Chemistry: Training Manual (4th Edition)," Moscow MEDpress-inform, 2007, pp. 27-29 (with Machine translation).

Extended European Search Report in European Appln. No. 21863852.6, mailed on Aug. 7, 2024, 10 pages.

Joshi et al., "Histone deacetylase inhibitors prevent pulmonary endothelial hyperpermeability and acute lung injury by regulating heat shock protein 90 function," American Journal of Physiology—Lung Cellular and Molecular Physiology, Dec. 2015, 309(12):L1410-L1419.

Kholodov et al., "Clinical Pharmacokinetics," Moscow Medicine, 1985, pp. 83-98, 134-138, and 378-380 (with Machine translation).

Leus et al., "HDAC 3-selective inhibitor RGFP66 demonstrates anti-inflammatory properties in RAW 264.7 macrophages and mouse precision-cut lung slices by attenuating NFKB p65 transcriptional activity," Biochemical Pharmacology, Mar. 2016, 108:58-74.

Liu et al., "HDAC6 inhibition blocks inflammatory signaling and caspase-1 activation in LPS-induced acute lung injury," Toxicology and Applied Pharmacology, Mar. 2019, 370:178-183 (Author Manuscript).

Lyu et al., "HDAC inhibitors as antifibrotic drugs in cardiac and pulmonary fibrosis," Therapeutic Advances in Chronic Disease, Jan. 2019, 10:1-19.

Yoon et al., "HDAC Inhibitors: Therapeutic Potential in Fibrosis-Associated Human Diseases," International Journal of Molecular Sciences, Mar. 2019, 20(6):1329, 15 pages.

Akgedik et al., "Effect of Resveratrol on Treatment of Bleomycin-Induced Pulmonary Fibrosis in Rats," Inflammation, Jun. 17, 2012, 35:1732-1741.

Ashcroft et al., "Simple method of estimating severity of pulmonary fibrosis on a numerical scale," J Clin Pathol, 1988, 41:467-470.

Balaji et al., "Biochanin-A ameliorates pulmonary fibrosis by suppressing the TGF-β mediated EMT, myofibroblasts differentiation and collagen deposition in in vitro and in vivo systems," Phytomedicine, Nov. 2020, 16 pages.

Balaji et al., "Role of the Drug Transporter ABCC3 in Breast Cancer Chemoresistance," PloS one, May 12, 2016, 22 pages.

Barnes et al., "Anti-inflammatory actions of steroids: molecular mechanisms," Trends Pharmacol Sci., Dec. 1993, 14:436-441.

George et al., "Pulmonary fibrosis and COVID-19: the potential role for antifibrotic therapy," The Lancet Respir. Med., Aug. 2020, pp. 807-815.

Khilnani et al., "Corticosteroids and ARDS: A review of treatment and prevention evidence," Lung India: official organ of Indian Chest Society, Jun. 2011, 28(2):114-119.

Korfei et al., "Comparison of the antifibrotic effects of the pan-histone deacetylase- inhibitor panobinostat versus the IPF-drug pirfenidone in fibroblasts from patients with idiopathic pulmonary fibrosis," PLoS One, Nov. 27, 2018, 31 pages.

Richeldi et al., "Idiopathic pulmonary fibrosis," The Lancet, Mar. 29, 2017, 389(10082):1941-1952.

Roy et al., "Immunologic Therapy for ARDS, Septic Shock, and Multiple-Organ Failure," Clinical Implications of Basic Research, Mar. 1993, 103(3):932-943.

Saito et al., "HDAC8 inhibition ameliorates pulmonary fibrosis," Am.J of Physiol. Lung cellular molecular physiology, 2019, 316(1):L175-L186.

Saito et al., "Tubastatin ameliorates pulmonary fibrosis by targeting the TGFβ-PI3K-Akt pathway," PloS one, Oct. 18, 2017, 17 pages.

Shu et al., "Myofibroblast transdifferentiation: The dark force in ocular wound healing and fibrosis," Progress in retinal and eye research, Sep. 2017, 51 pages.

Spagnolo et al., "Pulmonary fibrosis secondary to COVID-19: a call to arms?" The Lancet Respir. Med, Aug. 2020, pp. 750-752.

Tang et al., "Histone deacetylases as targets for treatment of multiple diseases," Clinical science, Jun. 2013, 22 pages.

Uckun et al., "Selectively targeting TGF-β with Trabedersen/OT-101 in treatment of evolving and mild ARDS in COVID-19," Clin. Invest. (Lond.), May 31, 2020, 10(2):35-44.

Wu et al., "Risk Factors Associated With Acute Respiratory Distress Syndrome and Death in Patients With Coronavirus Disease 2019 Pneumonia in Wuhan, China," JAMA Intern Med., Jul. 2020, 180(7):1-11.

Zaghloul et al., "Attenuation of Bleomycin-induced pulmonary fibrosis in rats by flavocoxid treatment," Egypt. J. Basic Appl. Sci., Nov. 2, 2017, pp. 256-263.

International Search Report and Written Opinion in International Appln. No. PCT/IN2021/050851, mailed on Dec. 6, 2021, 10 pages.

International Preliminary Report on Patentability in International Appln. No. PCT/IN2021/050851, mailed on Mar. 16, 2023, 8 pages.

Khabele, "The therapeutic potential of class 1 selective histone deacetylase inhibitors in ovarian cancer," Frontiers in Oncology, May 2014, 4:111, 8 pages.

Schuetze et al., "Overlapping and Divergent Actions of Structurally Distinct Histone Deacetylase Inhibitors in Cardiac Fibroblasts," The Journal of Pharmacology and Experimental Therapeutics, Apr. 2017, 361(1):140-150.

* cited by examiner (8A)

(8B)

(8C)

(10A)                                        (10B)

**Effect of COMPOUND-108 and
109 on Pulmonary fibrosis genes**

Sham Control
Bleomycin control
Pirfenidone (75 mg/kg)
NINTD (100 mg/kg)
COMPOUND-109 (0.375mg/kg)
COMPOUND-109 (0.75mg/kg)
COMPOUND-109- (0.75mg/kg-BID)
COMPOUND-109 (1.5mg/kg)
COMPOUND-108 (0.75mg/kg)BID
COMPOUND-108 (0.75mg/kg)

(10C)

(A)    Histo-Pathology (H&E) Observation

Sham Control    Bleomycin control    Prfenidone-50mg/kg    COMPOUND-108 3mg/kg    COMPOUND-108 1.5mg/kg    COMPOUND-109 3mg/kg    COMPOUND-109 1.5mg/kg

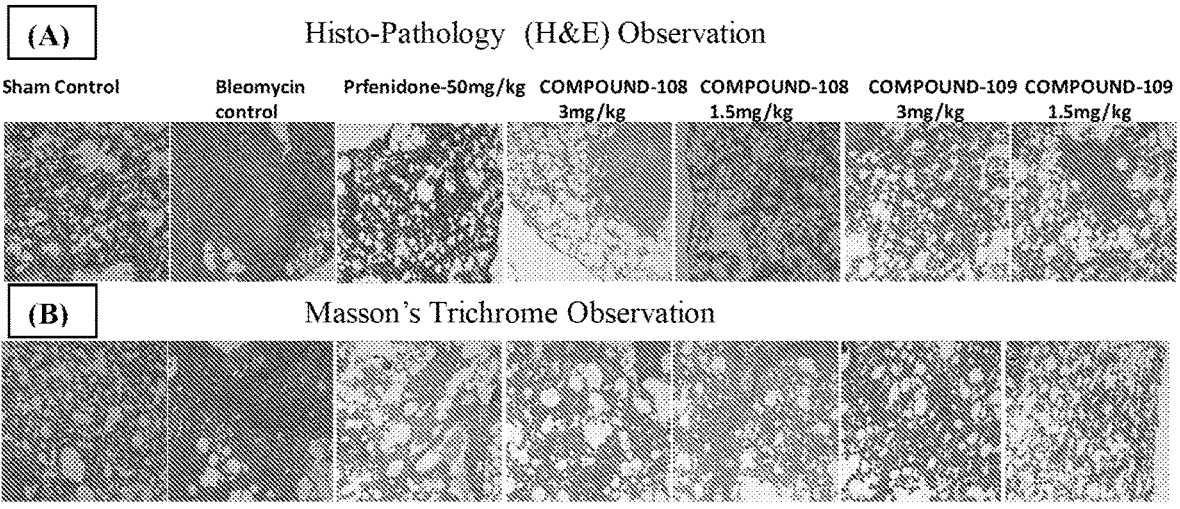

(B)    Masson's Trichrome Observation

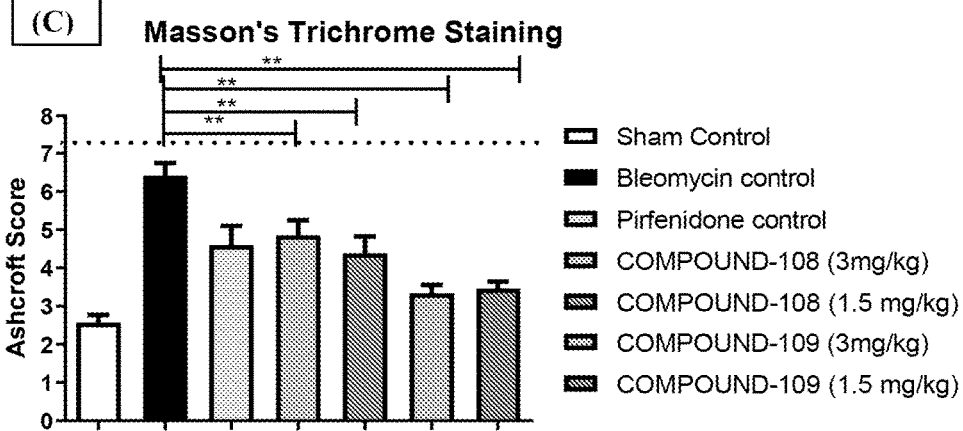

Images at 10X (C)    Masson's Trichrome Staining

Ashcroft Score

- ☐ Sham Control
- ■ Bleomycin control
- ▦ Pirfenidone control
- ▦ COMPOUND-108 (3mg/kg)
- ▨ COMPOUND-108 (1.5 mg/kg)
- ▦ COMPOUND-109 (3mg/kg)
- ▨ COMPOUND-109 (1.5 mg/kg)

Figure 11

(A)
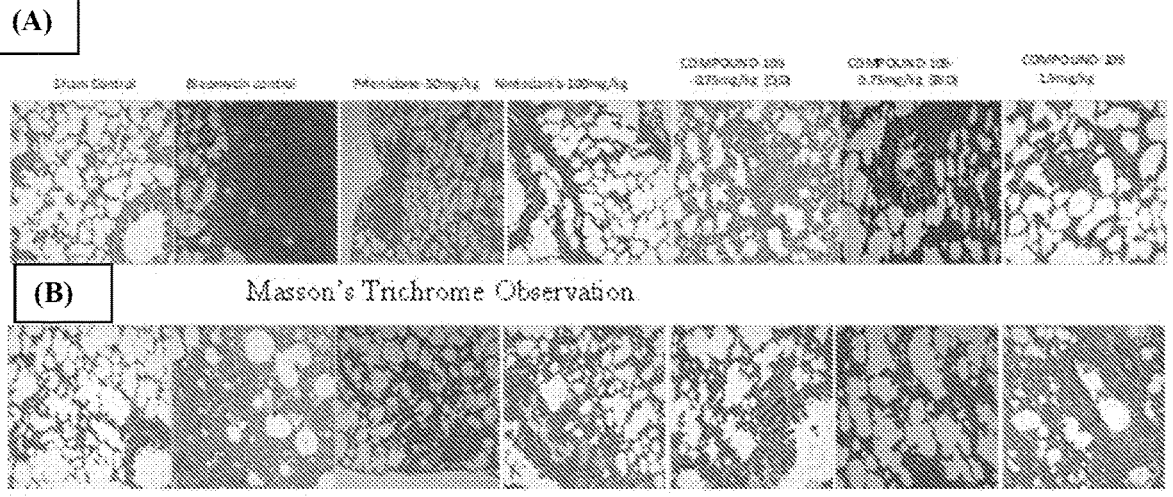
(B)    Masson's Trichrome Observation
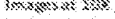
Images at 100X
(C)    Masson's Trichrome Staining
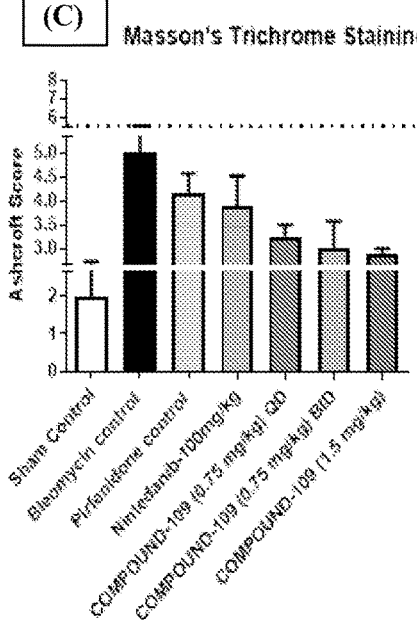
Figure 12

(13A)

(13B)

(13C)

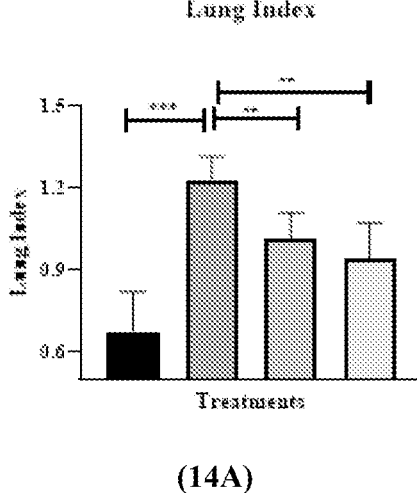
(14A)
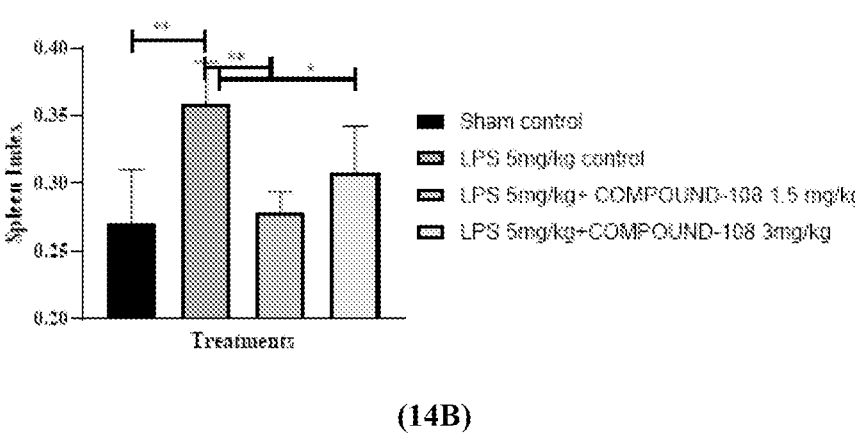
(14B)
Figure 14

(16A)

(16B)

(16C)

IL-6 levels at 6<sup>th</sup> hour
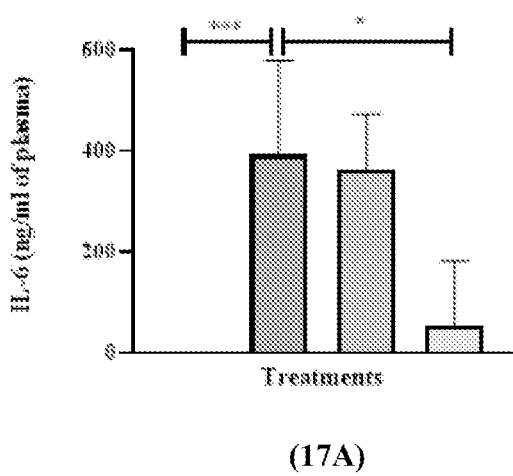
(17A)
IL-6 levels at 24<sup>th</sup> hour
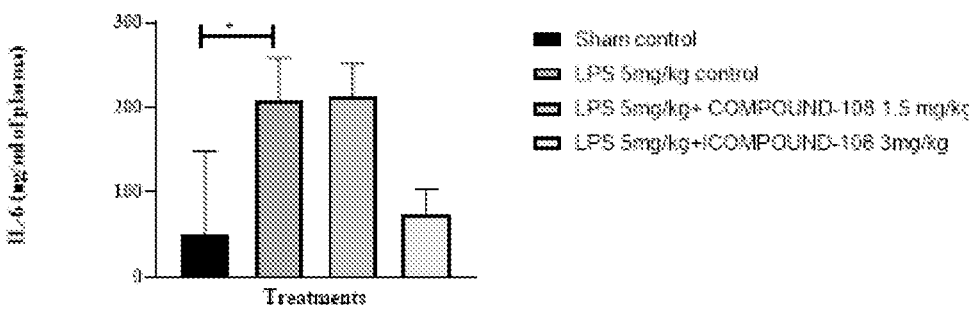
(17B)
Figure 17

(18A)

(18B)

HDAC INHIBITORS FOR IDIOPATHIC PULMONARY FIBROSIS AND OTHER LUNG INFLAMMATORY DISORDERS

CROSS REFERENCE OF RELATED APPLICATIONS

This application is a U.S. National Phase application under 35 U.S.C. § 371 of International Patent Application No. PCT/IN2021/050851, filed on Sep. 3, 2021, which claims the priority of Indian Patent Application No. 202011038497, filed on Sep. 5, 2020, the disclosure of which is incorporated herein by reference in its entirety.

FIELD OF THE INVENTION

The present invention relates to the series of compounds for the treatment of conditions selected from a group consisting of lung inflammatory disorders related to cytokine storm such as Acute lung injury, Acute respiratory distress syndrome (ARDS) and chronic lung disorders such as Idiopathic pulmonary fibrosis and other fibrotic disorders such as hepatic fibrosis, cardiac fibrosis, and kidney fibrosis.

BACKGROUND OF THE INVENTION

There are currently no effective prophylactic or post-exposure therapies. In patients infected with SARS-CoV-2, it has been described that disease severity and outcomes are related to the characteristics of the immune response. Interleukin IL-6 and other components (TNFα, IFNγ, MIP1α, IL-10, IL-1β, IL-12p40, IL-17A, IL-2, and IL8) of the inflammatory cascade contribute to host defence against infections.

Evidences from literature[1–4] have stated that the infections caused by some of the deadly viruses (like β-coronavirus) led to development of pulmonary fibrosis and ARDS. The underlying mechanism is associated with cytokine storm (ARDS) where cytokines like interleukins[2,7,10], granulo-cyte-colony stimulating factor, interferon-γ-inducible protein, monocyte chemo-attractant protein, macrophage inflammatory protein-α, tumor necrosis factor α are over produced[3,4] and it was known that, all these markers are highly up-regulated in fibrosis (Scar tissue formation). Over-time, the fibrotic tissue can destroy the normal lung and make it hard for oxygenating the blood.

Interleukin (IL)-6 and other components of the inflammatory cascade contribute to host defence against infections. However, exaggerated synthesis of IL-6 can lead to an acute severe systemic inflammatory response known as cytokine release syndrome (CRS). In the pathogenesis of SARS-CoV-2 pneumonia, a study found that a CRS involving a considerable release of proinflammatory cytokines occurred, including IL-6, IL-12, and tumor necrosis factor α (TNF-α). From the existing data, acute or chronic infections caused by bacterial or virus led to severe injury followed by ARDS (Acute respiratory distress syndrome) and pulmonary fibrosis.

Idiopathic pulmonary fibrosis (IPF) is a type of pulmonary disorder that results in scarring of the lungs for an unidentified reason. IPF is a form of interstitial lung disease, primarily causing inflammation in lung tissue and space surrounding the air sacs of the lungs ultimately causing thickened, stiff tissue formation that led to difficulty in breathing. Apart from its poor prognosis, it was also reported that there is 2-5 years of survival after diagnosis of the IPF[5]. Recent data on COVID-19 suggested that there could be substantial fibrotic consequences following SARS-CoV-2 infection[2,3]. Given the scale of the pandemic, the burden of IPF following SARS-CoV-2 infection is likely to be high, hence developing new anti-fibrotic agents may help in such situations. Therefore, there is an immediate need for the development of effective treatment against IPF.

ARDS is a life-threatening inflammatory lung injury characterized by severe acute hypoxemia, respiratory distress and pulmonary edema. In spite of the advances in ventilator and circulation therapy, it is reported that the mortality rate of patients with ARDS still remains high (exceeds 50%). Due to the non-availability of first-line treatment for ARDS, glucocorticoid anti-inflammatory steroids, which are very potent immunosuppressive agents, have been in use for ARDS from several decades and their outcomes have not been proven to be beneficial[6,8]. Even high-dose glucocorticoid therapy of patients at risk of developing ARDS neither improved the clinical outcome nor reversed ARDS progression[7,8].

Role of HDAC Inhibitors in IPF and Other Lung Disorders

Histone deacetylease inhibitors (HDACi) are the therapeutic agents used against cancer and many other diseases including fibrotic disorders[9]. Lungs with IPF exhibit distinct expression patterns of HDACs especially HDAC8 and HDAC6. In lungs with IPF, HDAC8/HDAC6 expression is noticed in myofibroblasts, and vascular smooth and bron-chiolar epithelial cells. It was reported that HDAC-8 and HDAC-6 levels were highly up-regulated in IPF patient samples[10,11]. The present disclosure provides therapeutic potential of HDAC inhibitors against pulmonary fibrosis, ARDS and other lung injuries caused by infections acting through reducing the cytokine storm, the pro-inflammatory cytokine levels, inflammation and epithelial to mesenchymal transition (EMT), extra cellular matrix (ECM) production, collagen deposition, and modulating the disturbed (thickened alveolar walls and Interstitial inflammation) lung architecture.

SUMMARY OF THE INVENTION

The present invention provides HDACi compounds which relates to indole based sulfonyl hydroxamic acid of formula 1 (below), useful for preventing or treating ARDS. The present invention provides a new use of the HDACi compounds for preventing or treating IPF, ARDS and lung injury.

The present invention provides a prophylactic or therapeutic agent for IPF and ARDS, which comprises the HDACi compounds.

The present invention provides a compound of formula 1 for treating impaired function of lung, reduction of collagen deposition and reduction of pulmonary fibrosis.

In an aspect of the present disclosure, there is provided a sulfonyl hydroxamine acid compounds of general formula 1

Formula 1

3 wherein

Ring A and B are independently selected from aryl, heteroaryl, cycloalkyl, fused aryl, or fused alkyl group;

$R_1$, $R_2$, $R_3$, $R_4$, $R_5$, $R_6$ and $R_7$ are independently selected from hydrogen, alkoxy, aryloxy, hydroxy, ester, amide, amino, alkyl, aryl, heteroaryl, halogen, nitro, cyano, and aldehyde; and X is O, for use in the treatment of condition selected from a group consisting of lung inflammatory disorders, and fibrotic disorders.

In a second aspect of the present disclosure, there is provided a sulfonyl hydroxamine acid compounds as disclosed herein, for the application in condition selected from a group consisting of lung inflammatory disorders (ARDS and acute lung injury), and fibrotic disorders (Pulmonary fibrosis), wherein the structural formulas of the representative compounds comprises of: COMPOUND-107, COMPOUND-108, COMPOUND-109, and COMPOUND-110:

107

108

109

4

-continued

110

In a third aspect of the present disclosure, there is provided a method for treatment of condition selected from a group consisting of IPF, hepatic fibrosis, impaired functions of lung and liver, with the sulfonyl hydroxamine acid compounds as disclosed herein, and/or their formulation with or without other ingredients.

These and other features, aspects, and advantages of the present subject matter will be better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter.

BRIEF DESCRIPTION OF THE DRAWINGS

FIG. 11 depicts the effect of COMPOUND-108 and 109 against BLM induced inflammatory changes in lung tissues (H&E and Masson's trichrome staining).

FIG. 12 depicts the effect of COMPOUND-108 and 109 against BLM induced inflammatory changes in lung tissues (H&E and Masson's trichrome staining).

FIG. 14 depicts the effect of COMPOUND-108 against LPS increased Lung and spleen indices

FIG. 17 depicts the effect of COMPOUND-108 against LPS increased levels of IL-6 levels in plasma samples of the rats.

DETAILED DESCRIPTION OF THE INVENTION

Figure 1:
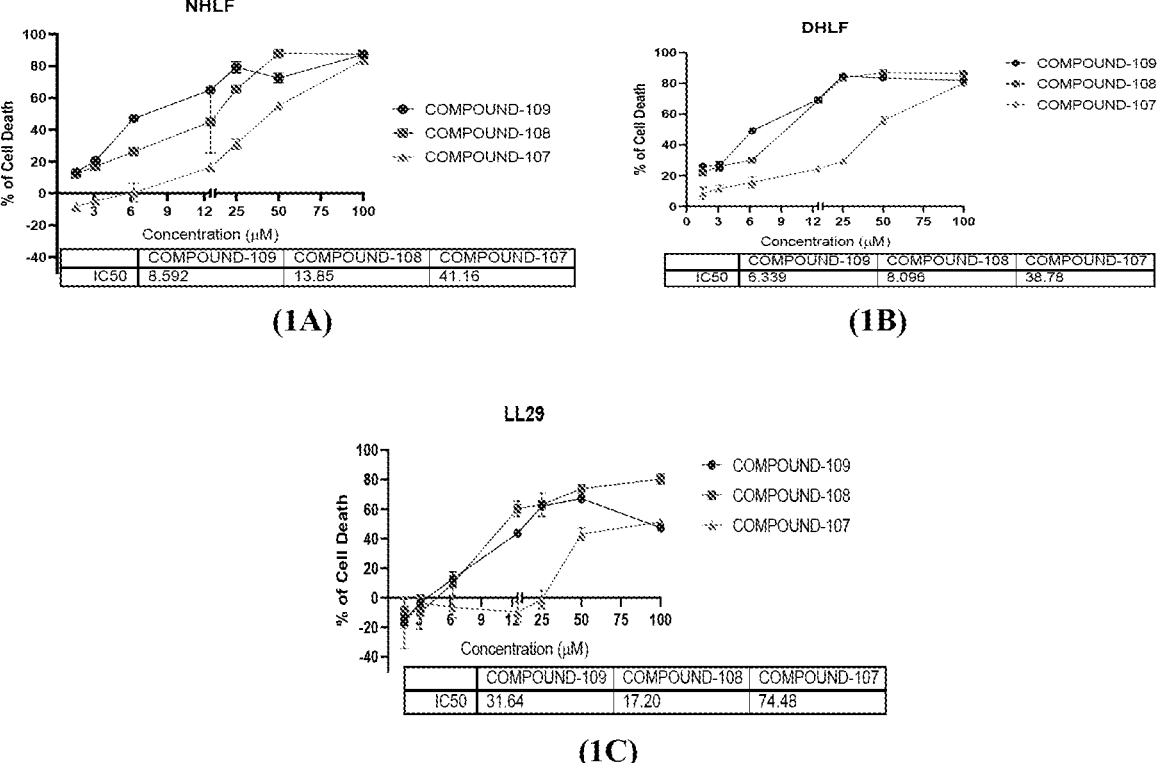
FIG. 1 depicts the cell viability of test compounds against NHLF, DHLF and LL29 cells. It shows the $IC_{50}$ of COMPOUND-109, COMPOUND-108 and COMPOUND-107.

The invention will now be described in detail in connection with certain preferred and optional embodiments, so that various aspects thereof may be more fully understood and appreciated.

Definitions:

For convenience, before further description of the present disclosure, certain terms employed in the specification, and examples are delineated here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only".

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

The term "alkyl" refers to a saturated hydrocarbon chain having the specified number of carbon atoms. For example, which is not limited, alkyl group having from 1-6 carbon atoms, or 1-4 carbon atoms. Alkyl groups may be straight or branched chained groups. Representative branched alkyl groups have one, two, or three branches. Preferred alkyl groups include, without limitation, methyl, ethyl, n-propyl, isopropyl, butyl, isobutyl, and t-butyl.

The term "alkoxy" refers to an alkyl group attached via an oxygen linkage to the rest of the molecule. For example, which is not limited, alkoxy refers to an alkyl group having from 1-6 carbon atoms, or 1-4 carbon atoms attached via an oxygen linkage to the rest of the molecule. Preferred alkoxy groups include, without limitation, —OCH$_3$ (methoxy), —OC$_2$H$_5$ (ethoxy) and the like.

The term "halogen" refers to a halogen radical, for example, fluoro, chloro, bromo, or iodo.

The term "aryl" refers to an aromatic ring having a specified number of carbon atoms. For example, an aryl group having 6 to 15 member atoms, or 6 member atoms. Preferred aryl groups include, without limitation, phenyl, naphthyl, and the like.

The term "heteroaryl" refers to aromatic rings containing from 1 to 5 heteroatoms in the ring. "Heteroaryl" groups may be substituted with one or one or more substituents if so defined herein. For example, which is not limited, heteroaryl rings having 1 to 15 carbon(s) as member atoms. The "heteroaryl" includes pyridinyl, tetrazolyl, or pyrazolyl. "Heteroatom" refers to a nitrogen, sulfur, or oxygen atom, for example, a nitrogen atom or an oxygen atom.

The term "cycloalkyl" refers to a saturated hydrocarbon ring having a specified number of carbon atoms, which may be monocyclic or polycyclic. For example, which is not limited, C$_{3-15}$ cycloalkyl refers to a cycloalkyl group having from 3 to 15 member atoms. For example, which is not limited, cycloalkyl group having from 3 to 15 membered atoms. Preferred cycloalkyl groups include, without limitation, cyclopropyl, cyclobutyl, cyclopentyl, cyclohexyl, cyclooctanyl, and the like.

The term "amide" refers to C(O)NH group attached via a carbonyl linkage to the rest of the molecule.

The term "hydroxy" refers to O—H moiety attached via an oxygen linkage to the rest of the molecule.

The present disclosure is not to be limited in scope by the specific embodiments described herein, which are intended for the purposes of exemplification only. Functionally-equivalent products, compositions, and methods are clearly within the scope of the disclosure, as described herein.

In an embodiment of the present disclosure, there is provided a sulfonyl hydroxamine acid compound of formula 1

Formula 1 wherein ring A and B are independently selected from aryl, heteroaryl, cycloalkyl, fused aryl, or fused alkyl group; R$_1$, R$_2$, R$_3$, R$_4$, R$_5$, R$_6$ and R$_7$ are independently selected from hydrogen, alkoxy, aryloxy, hydroxy, ester, amide, amino, alkyl, aryl, heteroaryl, halogen, nitro, cyano, and aldehyde; and X is O, for use in the treatment of condition selected from a group consisting of lung inflammatory disorders, and fibrotic disorders.

In an embodiment of the present disclosure, there is provided a sulfonyl hydroxamine acid compound of formula 1 as disclosed herein, for use in the treatment of condition selected from a group consisting of lung inflammatory disorders (ARDS and acute lung injury), and fibrotic disorders (Pulmonary fibrosis), wherein the structural formulae of the representative compound comprises of:

107

108

109

110

In an embodiment of the present disclosure, there is provided a sulfonyl hydroxamine acid compound of formula 1 as disclosed herein, for use in the treatment of condition selected from a group consisting of lung inflammatory disorders, and fibrotic disorders, wherein the sulfonyl hydroxamine acid compounds are comprised of: 4-(N-(3-(3-fluoro-5-hydroxyphenyl)-1-methyl-1H-indol-5-yl)sulfamoyl)-N-hydroxyl benzamide (107), 4-(N-(3-(3-chlorophenyl)-1-methyl-1H-indol-5-yl)sulfamoyl)-N-hydroxybenzamide (108), 4-(N-(3-(6-ethoxypyridin-3-yl)-1-methyl-1H-indol-5-yl)sulfamoyl)-N-hydroxy benzamide (109), N-hydroxy-4-(N-(1-methyl-3-(2,4,5-trifluorophenyl)-1H-indol-5-yl)sulfamoyl) benzamide (110).

In another embodiment of the present disclosure, there is provided a sulfonyl hydroxamine acid compound of formula 1 as disclosed herein, for the application in condition selected from a group consisting of lung inflammatory disorders, and fibrotic disorders, wherein the sulfonyl hydroxamine acid compound comprises of: 4-(N-(3-(3-chlorophenyl)-1-methyl-1H-indol-5-yl)sulfamoyl)-N-hydroxybenzamide (108).

In an embodiment of the present disclosure, there is provided a sulfonyl hydroxamine acid compound of formula 1 as disclosed herein, with the effective dose for use in the treatment of condition selected from a group consisting of lung inflammatory disorders and fibrotic disorders, wherein the lung inflammatory disorders related to cytokine storm such as Acute lung injury, Acute respiratory distress syndrome (ARDS), Idiopathic pulmonary fibrosis, and the fibrotic disorders such as hepatic fibrosis, cardiac fibrosis, and kidney fibrosis.

In an embodiment of the present disclosure, there is provided a sulfonyl hydroxamine acid compound of formula 1 as disclosed herein, with the effective dose for use in the treatment of condition selected from a group consisting of lung inflammatory disorders, and fibrotic disorders, wherein the compound significantly attenuate the lipopolysaccharides (LPS) induced infiltration of WBC and Neutrophils.

In an embodiment of the present disclosure, there is provided a sulfonyl hydroxamine acid compound of formula 1 as disclosed herein, with the effective dose for use in the treatment of condition selected from a group consisting of lung inflammatory disorders and fibrotic disorders, wherein the compound significantly attenuate the LPS induced Lung volume (index), and spleen Indices.

In an embodiment of the present disclosure, there is provided a sulfonyl hydroxamine acid compound of formula 1 as disclosed herein, with the effective dose for use in the treatment of condition selected from a group consisting of lung inflammatory disorders, and fibrotic disorders, wherein the compound significantly reduces the expression of inflammatory markers consisting of pro-inflammatory cytokines (IL-6, IL-1β and IL-8), and chemokines (CCL2 and CCL-7) along with chemokine ligands (CXCL-6, CXCL-10 and CXCL-11), and TLR3 genes.

In an embodiment of the present disclosure, there is provided a sulfonyl hydroxamine acid compound of formula 1 as disclosed herein, with the effective dose for use in the treatment of condition selected from a group consisting of lung inflammatory disorders and fibrotic disorders, wherein the compound attenuate the LPS induced IL-6 levels in plasma samples.

In an embodiment of the present disclosure, there is provided a sulfonyl hydroxamine acid compound of formula 1 as disclosed herein, with the effective dose for use in the treatment of condition selected from a group consisting of lung inflammatory disorders and fibrotic disorders, wherein COMPOUND-108 most effectively ameliorated the lung pathological conditions.

In an embodiment of the present disclosure, there is provided a sulfonyl hydroxamine acid compound of formula 1 as disclosed herein, with the effective dose for use in the treatment of condition selected from a group consisting of lung inflammatory disorders and fibrotic disorders, wherein the compound significantly attenuated the extra cellular matrix proteins, collagen, and epithelial to mesenchymal markers expression in TGF-β stimulated LL29, DHLF, and NHLF cells.

In an embodiment of the present disclosure, there is provided a sulfonyl hydroxamine acid compound of formula 1 as disclosed herein, with the effective dose for use in the treatment of condition selected from a group consisting of lung inflammatory disorders and fibrotic disorders, wherein the compound significantly mitigated the inflammatory markers expression and infiltration of neutrophils in BLM challenged rats.

In an embodiment of the present disclosure, there is provided a sulfonyl hydroxamine acid compound of formula 1 as disclosed herein, with the effective dose for use in the treatment of condition selected from a group consisting of lung inflammatory disorders and fibrotic disorders, wherein the compound significantly reduced the lung index and hydroxyproline levels in BLM challenged rats.

In an embodiment of the present disclosure, there is provided a sulfonyl hydroxamine acid compound of formula 1 as disclosed herein, with the effective dose for use in the treatment of condition selected from a group consisting of lung inflammatory disorders and fibrotic disorders, wherein the compound significantly attenuated the fibrotic markers expression in BLM challenged rats.

In an embodiment of the present disclosure, there is provided a sulfonyl hydroxamine acid compound of formula 1 as disclosed herein, with the effective dose for use in the treatment of condition selected from a group consisting of lung inflammatory disorders and fibrotic disorders, wherein COMPOUND-108 most effectively ameliorated the fibrotic alterations in BLM challenged rat lung tissues.

In an embodiment of the present disclosure, there is provided a sulfonyl hydroxamine acid compound of formula 1 as disclosed herein, with the effective dose for use in the treatment of condition selected from a group consisting of lung inflammatory disorders and fibrotic disorders, wherein the effective dose ranges between 2 mg/kg to 4 mg/kg body weight.

In an embodiment of the present disclosure, there is provided use of the sulfonyl hydroxamine acid compound of formula 1 as disclosed herein, in the treatment of condition selected from lung inflammatory disorders and fibrotic disorders.

EXAMPLES

Following examples are given by way of illustration and therefore should not be construed to limit the scope of the invention.

Methodology

Cell-Lines and Cell Culture

LL29 cells (lung fibroblasts from IPF patient) were purchased from ATCC and cultured in Ham's F-12K medium supplemented with 15% FBS. Primary lung fibroblasts cells, NHLF and DHLF-IPF cells were purchased from LONZA and cultured in FGF-2 medium with FGF, Insulin and FBS. All the cells were maintained in a humidified atmosphere of 95% air with 5% $CO_2$ at 37° C.

Sulphorhodamine-B Assay (Cytotoxicity Assay)

Cells (LL29, NHLF and DHLF-IPF) were seeded into a 96 well plate (8×103 cells/well) and cells were treated with HDAC-inhibitors (COMPOUND-109, COMPOUND-108 and COMPOUND-107) which were dissolved in DMSO, in various concentrations (0, 0.78, 1.56, 3.12, 6.25, 12.5,25, 50, 100 µM) and DMSO (vehicle control). Further the cells were incubated for 72 hours. Then, cell percentage of cell death was determined with sulforhodamine-B (Sigma Aldrich, St Louis, MI) assay. $IC_{50}$ values were calculated by curve fit method using GraphPad Prism-8 software.

TGF-β Stimulation/Hypoxia Induction

Cells were pre-treated with HDAC-inhibitors (COMPOUND-109, COMPOUND-108 and COMPOUND-107) for 2 hours in serum free media and then human recombinant TGF-β (R&D Systems, Minneapolis, MN) was added at a concentration of 5 ng/mL and cultured for 72 hours for all the experiments.

RNA Isolation, cDNA Synthesis and q-RT-PCR

RNA isolation was carried out using Trizol as described[12, 13]. RNA was isolated using Trizol-chloroform method and total RNA was quantified using nano-drop, 1 µg of RNA was used for cDNA synthesis using primescript cDNA synthesis kit (Takara bio) according to manufacturer's instructions. Primers for EMT (Fibronectin1 (FN1), Vimentin, α-SMA and Snail) markers, ECM markers (Timp1, Timp3 and LoxL2), Collagen markers (Collagen 1α1 (Col1) and Collagen 3α1(col1) and housekeeping markers (β2M and β-actin) were designed using Primer 3 software and all primer sequences were listed in Table 1. Real time quantitative PCR (qRT-PCR) was carried out using SYBR green master mix and the differences in mRNA expression of all the gene levels were calculated as the fold change using the formula 2-ΔΔct. In all Q-RT-PCR data plots, vehicle control fold change was normalized to 1.

TABLE 1

Sequences of Transcripts/primers {human (h) and rat (R) mRNA} used for real-time quantitative PCR.

| S. No | Name of the gene | Forward primer Sequence | Reverse Primer Sequence |
|---|---|---|---|
| 1 | hSnail | ACCCCACATCCTTCTCACTG | TACAAAAACCCACGCAGACA |
| 2 | hTwist1 | GTCCGCAGTCTTACGAGGAG | CCAGCTTGAGGGTCTGAATC |
| 3 | h-FN1 | GGAAAGCATATGCAGCCAAC | CTACAGTATTGCGGGCCAGA |
| 4 | h-Vim | AACAACCGACACTCCTACAAGA | TGGTTGGATACTTGCTGGAAA |

TABLE 1-continued

Sequences of Transcripts/primers {human (h) and rat (R) mRNA} used for real-time quantitative PCR.

| S. No | Name of the gene | Forward primer Sequence | Reverse Primer Sequence |
|---|---|---|---|
| | | Genes associated with Extra cellular matrix formation | |
| 5 | h-αSMA: | GAAGAAGAGGACAGCACT | TCCCATTCCCACCATCAC |
| 6 | h-TIMP1 | CTTCTGGCATCCTGTTGTTG | GGTATAAGGTGGTCTGGTTG |
| 7 | h-TIMP3 | CCTGCTACTACCTGCCTTGC | GGCGTAGTGTTTGGACTGGT |
| 8 | h-LOXL-2 | CCGGGTGGAGGTGTACTATG | TCGTTGCCAGTACAGTGGAG |
| | | Genes associated with Collagen formation | |
| 9 | h-CTGF | CAAGGGCCTCTTCTGTGACT | ACGTGCACTGGTACTTGCAG |
| 10 | h-COL3α1 | CCAGGAGCTAACGGTCTCAG | CAGGGTTTCCATCTCTTCCA |
| 11 | h-Collagen1α1 | TGAGCCAGCAGATCGAGA | ACCAGTCTCCATGTTGCAGA |
| 10 | h-SMAD2 | GGAATTTGCTGCTCTTCTGG | TCTGCCTTCGGTATTCTGCT |
| 11 | h-VEGF-αA | CTACCTCCACCATGCCAAGT | GCAGTAGCTGCGCTGATAGA |
| 12 | h-TGF-□ | CCCAGCATCTGCAAAGCTC | GTCAATGTACAGCTGCCGCA |
| 13 | hHIF1α | GGACAAGTGACCACAGGA | GGAGAAAATCAAGTCGTG |
| 14 | h-β2M | AGGCTATCCAGCGTACTCCA | CGGATGGATGAAACCCAGACA |
| 15 | R-α-SMA (M/R) | GAGGCACCACTGAACCCTAA | CATCTCCAGAGTCCAGCACA |
| 16 | R-FN1 (M/R) | GAGGTGACAGAGACCACAA | CTGGAGTCAAGCCAGACACA |
| 17 | R-E-cadherin (M/R) | AAGGGCTTGGATTTTGAGG | AGATGGGGGCTTCATTCAC |
| 18 | R-TGF-β1 | TAATGGTGGACCGCAACAACG | GGCACTGCTTCCCGAATGTCT |
| 19 | R-COL1A I | TACAGCACGCTTGTGGATGG | CAGATTGGGATGGAGGGAGTT |
| 20 | R-CTGF | CCTGGTCCAGACCACAGAGT | TTTTCCTCCAGGTCAGCTTC |
| 21 | R-COL3A1 | AGATGCTGGTGCTGAGAAG | TGGAAAGAAGTCTGAGGAAGG |
| 22 | R-TIMP1 | ATCGCGGGCCGTTTAAGGA | CAAGGGATGGCTGAACAGGGA |
| 23 | R-α-SMA (M/R) | GAGGCACCACTGAACCCTAA | CATCTCCAGAGTCCAGCACA |
| 24 | R-FN1 (M/R) | GAGGTGACAGAGACCACAA | CTGGAGTCAAGCCAGACACA |
| 25 | R-Ecad | AAGGGCTTGGATTTTGAGG | AGATGGGGGCTTCATTCAC |
| 26 | R-βactin | CAGCTGAGAGGGAAATCGTG | CGTTGCCAATAGTGATGACC |
| 27 | Rat-CCL7 | 5'-GCATGGAAGTCTGTGCTGAA-3' | 5'-CCGTTCCTACCCCTTAGGAC-3' |
| 28 | Rat CXCL-8 (CXCL-1 or IL-8) | 5'-CCCCCATGGTTCAGAAGATTG-3' | 5'-TTGTCAGAAGCCAGCGTTCAC-3' |
| 29 | RAT IL-10 | 5'-GCAGGACTTTAAGGGTTACTTG-3' | 5'-GGGGAGAAATCGATGACAGC-3' |
| 30 | Rat-IL-6 | 5'-GCCCTTCAGGAACAGCTATGA3' | 5'-TGTCAACAACATCAGTCCCAAGA-3' |

TABLE 1-continued

Sequences of Transcripts/primers {human (h) and rat (R) mRNA} used for real-time quantitative PCR.

| S. No | Name of the gene | Forward primer Sequence | Reverse Primer Sequence |
|---|---|---|---|
| 31 | Mouse Cox-2 | 5'-CAGACAACATAAACTGCGCCTT-3' | 5'-GATACACCTCTCCACCAATGACC 3' |
| 32 | Rat Cox-2 | 5'-CCGGGTTGCTGGGGGAAGGA-3' | 5'-CCACCAGCAGGGCGGGATACAG-3' |
| 33 | Rat-TLR-3 | 5'-GCAACAACAACATAGCCAAC-3' | 5'-CCTTCAGGAAATTAACGGGAC-3' |
| 34 | Mouse TLR-3 | 5'-CCTCCAACTGTCTACCAGTTCC-3' | 5'-GCCTGGCTAAGTTATTGTGC-3' |
| 35 | Rat-Cxcl11 | 5'-AGATGAACAGGACGGGCAT-3' | 5'-GCTGCCATTTTGACCACTTTC-3' |
| 36 | Rat-Cxcl6 | 5'-GTTTGCTTAACCTTAGCTCCA-3' | 5'-GTTTTCTTATTTTCACTGCCC-3' |
| 37 | Rat-Cxcl10 | 5'-AGCCAACCTTCCAGAAGCACCA-3' | 5'-TCATGGAAGTCGATGCAGGTGC-3' |
| 38 | Rat-Ccl2 | 5'GCTACTCATTCACTGGCAAGA 3' | 5' CTTATTGGGGTCAGCACAGAT 3' |
| 39 | Rat-INF-□ | '5-CTGTTACTGCCAAGGCAC-3 | 5-TTTGCCAGTTCCTCCAGAT-3 |

Experimental Animals

Adult female Wistar rats (180-200 g, n=50) at the age of 8-10 weeks were used to develop bleomycin induced pulmonary fibrosis model. All animals were kept under constant environmental and nutritional conditions throughout the experimental period. The research protocol complies with the ethical guidelines of experimental research; "Institutional Animal Ethics Committee" (CPSCEA Registration No. 97/GO/RBi/S/1999/CPCSEA and study approval No. IICT/056/2019), CSIR-IICT, Hyderabad.

Induction of Pulmonary Fibrosis

Except 8 animals (Sham control), pulmonary fibrosis was induced in remaining all animals (32 Wistar rats) by intratracheal instillation of BLM (5 mg/kg) as sulfate salt dissolved in 1 mL of normal saline. Rats were anesthetized using ketamine and xylazine (80 mg/kg and 15 mg/kg respectively as per body weight, I.P.). BLM was administered intratracheally into the lungs of the rats.

Animal Grouping and Treatment

Pulmonary fibrosis was induced by a single intratracheal instillation of BLM (5 mg/kg) to the set of animals (n=40) excluding sham control animals (n=8)[14]. BLM was dissolved in saline to attain the concentration of 5 mg/ml. Animals were anesthetized with ketamine (80 mg/kg) and xylazine (10 mg/kg). BLM was administered intratracheal (5 mg/kg) to the anesthetized Wistar rats and saline was administered intratracheally in to sham control animals. Post BLM administration, body weight reduction was calculated (on 14th day) and the animals which showed body weight reduction (around 10%) were included in the study. Further, these animals were randomized into four groups (as described in Table-2) apart from sham control (8 rats/group). Table 2 represents the grouping pattern of animals.

| Group No. | Group Name | No of animals/ group |
|---|---|---|
| 1 | Sham control | 10 |
| 2 | Bleomycin Sulphate (5 U/kg) control | 10 |
| 3 | Bleomycin sulphate (5 U/kg) + Pirfenidone 75 mg/kg | 10 |
| 4 | Bleomycin sulphate (5 U/kg) + Nintedanib 100 mg/kg | 10 |
| 5 | Bleomycin sulphate (5 U/kg) + COMPOUND-109 (0.375 mg/kg) | 10 |
| 6 | Bleomycin sulphate (5 U/kg) + COMPOUND-109 (0.75 mg/kg) | 10 |
| 7 | Bleomycin sulphate (5 U/kg) + COMPOUND-109 (1.5 mg/kg) | 10 |
| 8 | Bleomycin sulphate (5 U/kg) + COMPOUND-109 (0.75 mg/kg-BID) | 10 |
| 9 | Bleomycin sulphate (5 U/kg) + COMPOUND-108 (0.75 mg/kg) | 10 |
| 10 | Bleomycin sulphate (5 U/kg) + COMPOUND-108 (0.75 mg/kg-BID) | 10 |

As described in the grouping pattern Table 2 and 3, animals were grouped and administered the compounds orally in the form of gum-acacia suspension (0.25%) daily for 14 days. Sham control (without bleomycin) animals were used as a control for bleomycin control (disease control) and administered everyday 0.5 mL of saline for 14 days orally. After the treatment period, BALF fluid was collected from 4 animals in each group and lungs were collected from another 4 animals for ex-vivo experiments and histopathological observations.

Treatment with COMPOUND-108 and Induction of ARDS in Male SD Rats:

Treatment group animals were treated with HDACi (COMPOUND-108) for 7 days at the doses of (1.5 mg/kg and 3 mg/kg), after the treatment period animals were subjected to ARDS instillation by intratracheally. Rats were anesthetized using ketamine and xylazine (80 mg/kg and 20 mg/kg, respectively as per body weight, I.P.). Except 8 animals (Sham control), ARDS was induced in remaining all animals (24 SD rats) by intratracheal instillation of Lipopolysachharide (5 mg/kg) dissolved in normal saline.

Table 3 represents the grouping pattern of animals.

| Groups. No | Groups | No. of animals | Pre-treatment |
|---|---|---|---|
| 1 | Sham control | 8 | |
| 2 | Disease Control (LPS by intra tracheal administration | 8 | |
| 3 | LPS + COMPOUND-108 1.5 mg/kg, p.o | 8 | 8 days |
| 4 | LPS + COMPOUND-108- 3 mg/kg, p.o | 8 | 8 days |

BALF Collection and Parameters Analysis

In 4 animals from each group, the thoracic cavity was opened and the tracheas were exposed, cannulated and 3 mL sterile 0.9% saline was slowly infused into the lungs. BALF was centrifuged at 2000 rpm, 4 ° C. for 10 min using cooling centrifuge. The sedimented cell pellets were pooled and re-suspended in 500 µl of sterile saline to quantify inflammatory cell counts; supernatant BLAF was examined for ALP and LDH parameters using auto-analyzer.

Hydroxy-Proline Assay

Collagen deposition was determined by measuring the total hydroxyproline content in wet lung tissue, which was measured by a hydroxyproline assay kit (abcam), according to the manufacturer's protocol. In brief, lungs were homogenized in sterile distilled water, alkalized using 10N NaOH and heated at 120° C. for 1 hour. Following alkaline hydrolysis samples were neutralized using 10N concentrated HCL. Then samples were into 96 well plate along with standards and kept for evaporation at 65° C. Then samples were oxidized by adding oxidation mixture followed by addition of developer and incubated at 37° C. for 5 min. Further, DMAB was added and incubated at 65° C. for 45 min and absorbance was measured Optical density at 560 nm using microplate reader. Concentration of total hydroxyproline (µg/µL) in the test samples is calculated[13].

Histopathology

A portion of the pulmonary lobe was harvested, rinsed with ice-cold phosphate buffer saline, and fixed with 10% neutral-buffered formalin, embedded in paraffin wax, sectioned (6 µm) and stained with H&E and Masson's trichrome. Three serial slices of 3 µm thickness each 50 µm apart of both lung lobes were stained with Masson's Trichrome. The slides were analyzed with a microscope in a random order using an (10×) objective. The severity of fibrosis and alveolitis in lung tissues (using H&E and Masson's trichrome staining) was semi-quantitatively assessed by a pathologist in a blinded fashion via Ashcroft scoring system[15]. The structural alterations of tissue were assessed based on the degree haemorrhage, emphysema, alveolar wall thickening, inflammatory lesions and collagen deposition or fibrosis[16].

Statistical Analysis

Statistical significance determined using student's t-test, ANOVA and two-way ANOVA. Curve-fit method was used to analyse $IC_{50}$ value. Graph-pad prism software version 8 was used for all statistical tests and plotting the graphs. Results are shown as mean±S.E.M. Error bars represent S.E.M., n=3. *p<0.05, p<0.01, *p<0.001. NS, non-significant.

Results on Pulmonary Fibrosis Model

EXAMPLE 1: Therapeutic Dose Determination for HDAC-Inhibitors

In vitro effects of HDAC-inhibitors (COMPOUND-109, COMPOUND-108 and COMPOUND-107) on cell viability were investigated on NHLF, DHLF and LL29 cells; $IC_{50}$ values were found to be in the range of 6.3±0.3, 74.74±0.22 µM in all three cell lines. Detailed $IC_{50}$ values were mentioned in FIGS. 1A, 1B and 1C. Based on the results of cell viability assay performed at various concentrations, safest doses were finalized for each cell line (Table 4) and re-tested. As expected, cell death was not observed at selected doses of HDAC-inhibitors.

Table 4 describes the concentration used for q-RT-PCR analysis.

| | Concentrations (in µM) of the HDAC inhibitor chosen for further experiments | | |
|---|---|---|---|
| | NHLF | DHLF | LL29 |
| COMPOUND-109 | 0.5 and 1 | 0.1, 0.25 and 1 | 1, 2.5 and 5 |
| COMPOUND-108 | 2.5 | 0.5, 1 and 2.5 | 1, 2.5, 5 and 10 |
| COMPOUND-107 | 5 and 10 | 1, 2.5 and 5 | 5, 10 and 20 |

Figure 2:
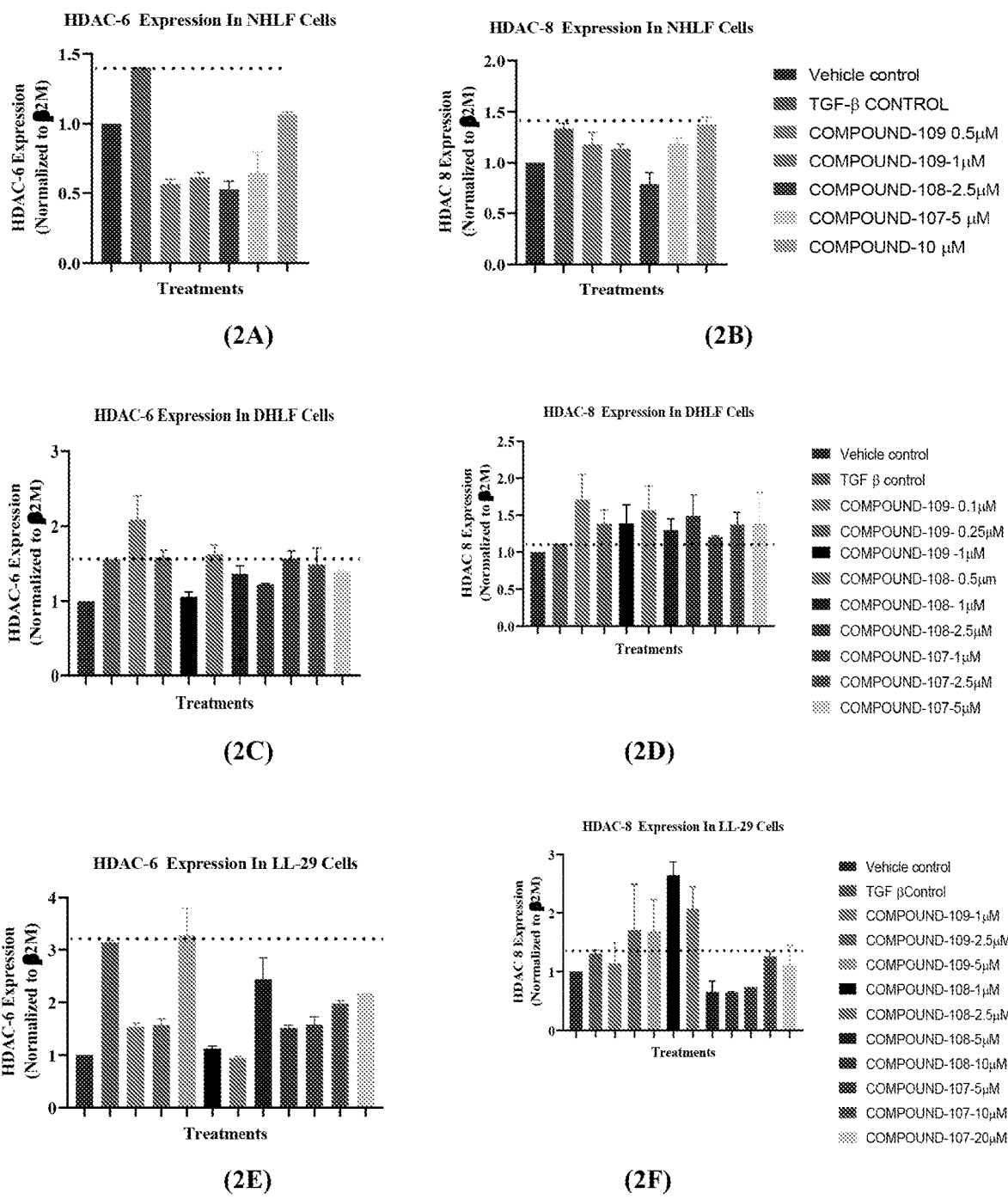
FIG. 2 depicts the expression levels of HDAC-8 and HDAC-6 upon treatment with IIC-T109, COMPOUND-108 and COMPOUND-107 in presence and absence of TGF-β1 in in 5 NHLF, DHLF and LL29 cells.

EXAMPLE 2: HDAC-Inhibitors Abrogated the TGF-β-Mediated Over Expression of HDAC-8 and HDAC-6 Levels HDAC-8 and HDAC-6 levels are known to increase upon TGF-β1 activation, BLM-induced pulmonary fibrosis and IPF patient samples (Ref). Since, the molecules are selective for HDAC-8 or 6, the effect of HDAC-inhibitors on gene expression of HDAC-8 and 6 was tested (FIG. 2). TGF-β1 stimulation enhanced (FIG. 2A-2F) the gene expression of HDAC-8 and HDAC-6 in NHLF, DHLF and LL29 cells. Upon treatment with HDAC inhibitors (COMPOUND-109, 108 and 107), HDAC-8 levels were reduced with COMPOUND-108 (concentration of 2.5 µM) in NHLF and LL29 cells. Other concentrations of Compound 108 or 109 or 107 did not modulate the HDAC-8 levels. In-contrast to HDAC-8 gene expression data, HDAC-6 gene expression levels were highly reduced in NHLF and LL29 with almost all the concentrations. However, in HDAC-6 levels were slightly down regulated in DHLF cells with highest concentrations of HDAC-inhibitors.

Hence, the results revealed that COMPOUND-108 potentially inhibits the HDCA-6 (2a) and HDAC-8 mRNA levels (2b), but COMPOUND-109, and COMPOUND-107 could inhibit only HDAC-6 mRNA levels (2a). Therefore, this demonstrated that COMPOUND-108 could be a dual inhibitor for HDAC-8 and HDAC-6. A few studies suggested that the dual or multi target HDAC inhibitors perform better to target the IPF compared to single/specific HDAC inhibitors[17].

Figure 3:
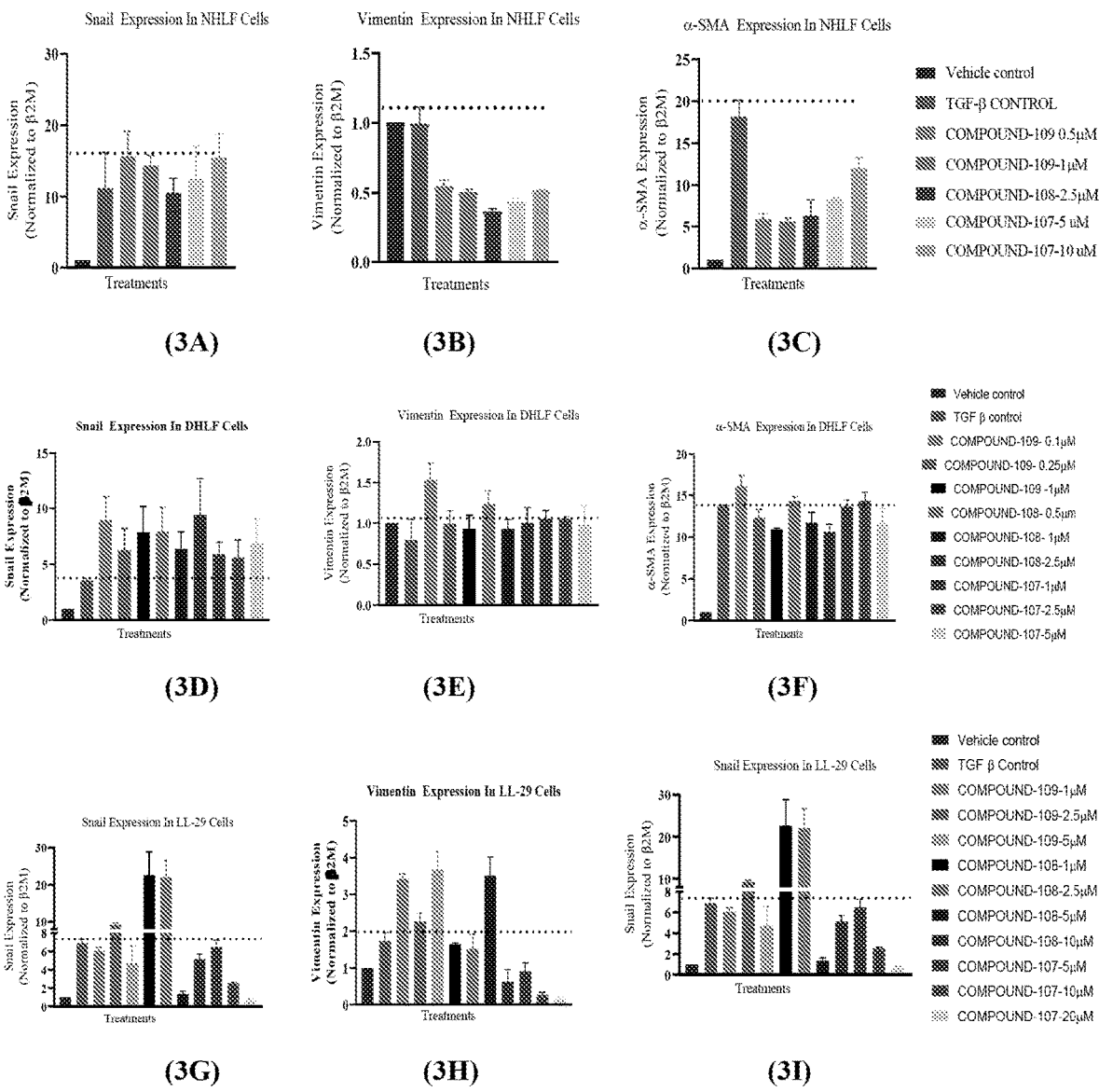
FIG. 3 depicts the expression levels of EMT markers (Snail, Vimentin and α-SMA) upon treatment with COMPOUND-109, COMPOUND-108 and COMPOUND-107 in presence and absence of TGF-β1 in NHLF, DHLF and LL29 cells.

EXAMPLE 3: HDAC-Inhibitors Ameliorated the TGF-β-Induced EMT Genes Expression in Cell Lines In in-vitro studies, TGF-β1 plays, a major role to induce EMT, which is driving force for myofibroblasts conversation[18]. Therefore, the effect of BCA on gene expression of EMT markers in TGF-β stimulated cells was investigated (FIG. 3e). TGF-β1 treated cells resulted in significant increase in the expression of EMT genes (Vimentin, Snail and α-SMA) (FIG. 3A-2I). Snail levels were highly down-regulated in LL29 cells upon treatment with COMPOUND-108 (5 and 10 μM) and COMPOUND-107 (10 and 20 μM). Treatment with Compound 109 or 108 or 107 showed that, vimentin and α-SMA levels were highly reduced in TGF-β1 stimulated NHLF and LL29 cells (FIGS. 3A-C and 3G-I), but, vimentin levels were not modulated with COM-POUND-109 (FIG. 3). In contrast to above results, HDAC-inhibitors did not modulate the EMT gene (Snail, Vimentin and α-SMA) expression levels in DHLF cells (FIG. 3D-3F). Taken together, HDAC-inhibitors potentially inhibit the EMT markers expression in Normal and IPF cells (LL29).

Figure 4:
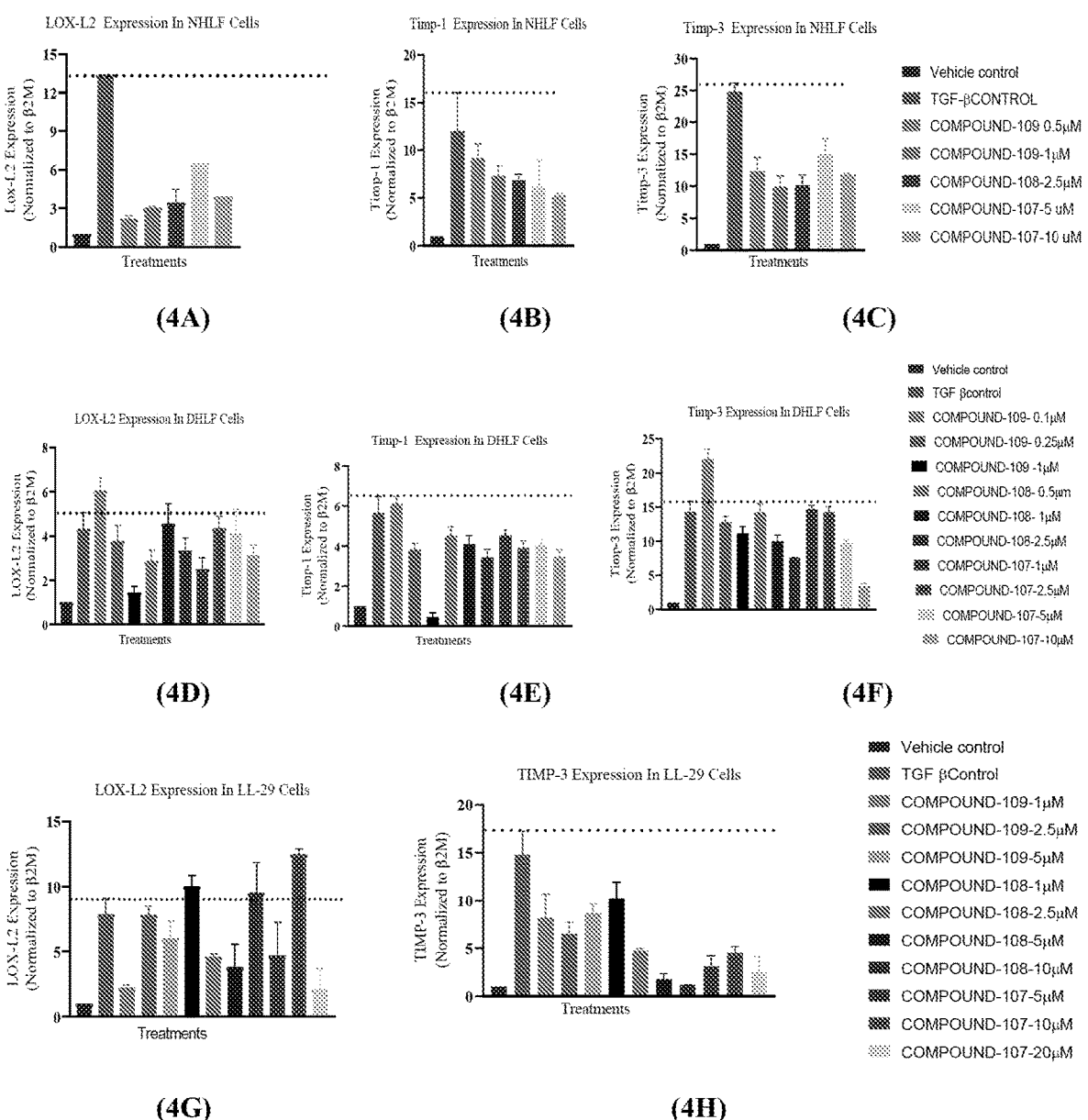
FIG. 4 depicts the expression levels of ECM markers (LOX-L2, Timp 1 and Timp3) upon treatment with COMPOUND-109, COMPOUND-108 and COMPOUND-107 in presence and absence of TGF-β1 in NHLF, DHLF and LL29 cells.
Figure 5:
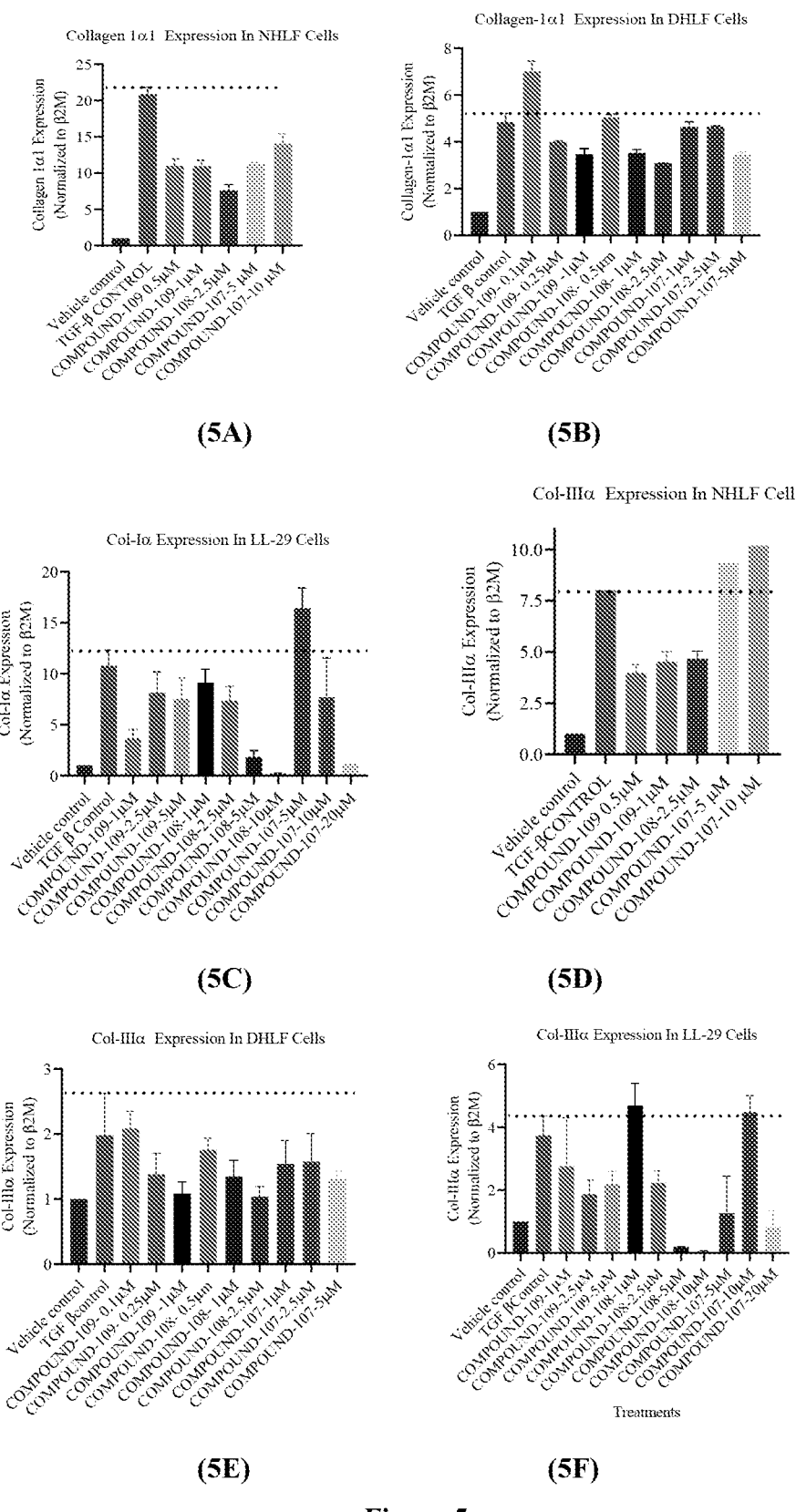
FIG. 5 depicts the expression levels of collagen associated markers (Collagen 1α1 and collagen 3α1) upon treatment with COMPOUND-109, COMPOUND-108 and COMPOUND-107 in presence and absence of TGF-β1 in NHLF, DHLF and LL29 cells.

EXAMPLE 4: HDAC-Inhibitors Abrogated the TGF-β-Induced ECM Production Genes Expression ECM plays a distinct role in organizing tissue architecture and regulation of cell function. This dynamic activity is controlled partly by matrix metalloproteinase (MMP) and tissue inhibitors of metalloproteinase (TIMPS). Therefore, the ECM markers (Timp1 and Timp3) and supporting mark-ers such as Lox-L2 were investigated (FIG. 4). TGF-β1 stimulation enhanced (FIG. 4A-4H) the gene expression of ECM markers. In line with EMT markers expression, HDAC-inhibitors treatment attenuated the expression Timp1, Timp3 and LoxL2 in NHLF (FIG. 4A-C), DHLF (FIG. 4D-4F) and LL29 (FIGS. 4G and 4I) cells in dose dependent manner. Overall, HDAC-inhibitors treatment potentially reduced the ECM marker expression in TGF-β1 stimulated fibroblast cells.

EXAMPLE 5: HDAC-Inhibitors Ameliorated the TGF-β-Induced Collagen Markers Expression in Cell Lines Further, the effect of HDAC-inhibitors on collagen depos-iting genes such as, Col1 and Col3 was investigated. TGF-β1 treatment highly up-regulated the gene expression of Col1 and col3 in NHLF, DHLF and L129 cells (FIG. 5A-5F). Interestingly, HDAC-inhibitors treatment also attenuated the TGF-β mediated collagen deposition marker expression in all cell types (FIG. 5A-5F) in dose dependent manner.

Figure 6:
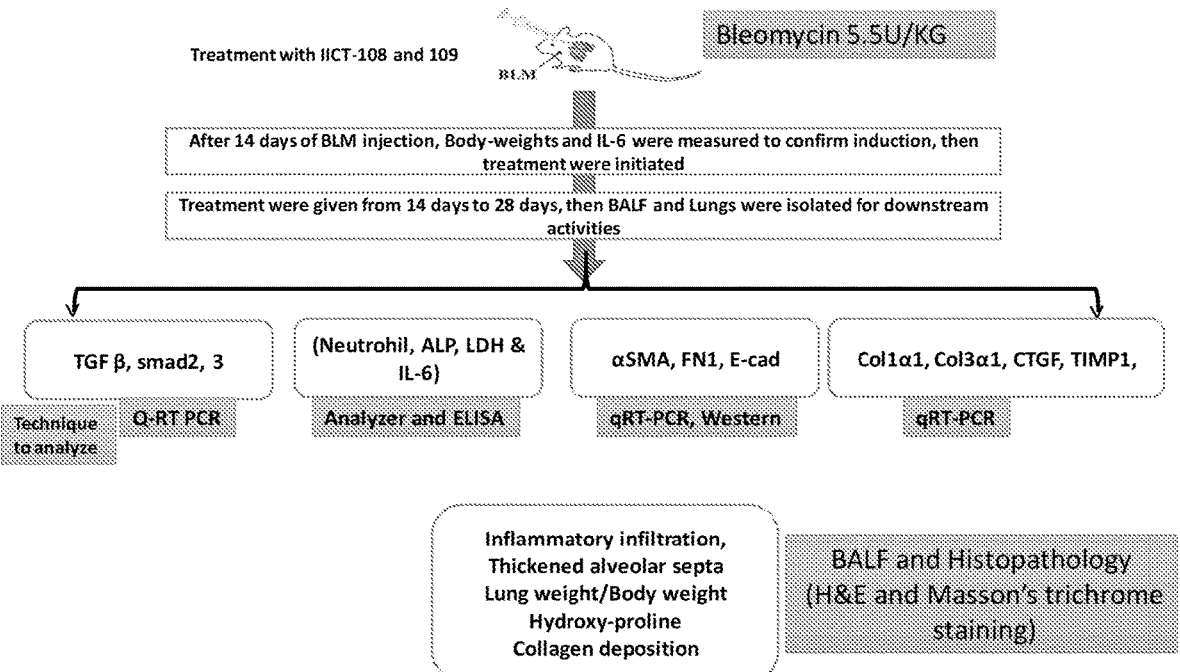
FIG. 6 depicts the schematic plan of BLM induced pulmonary fibrosis in rat model.
Figure 7:
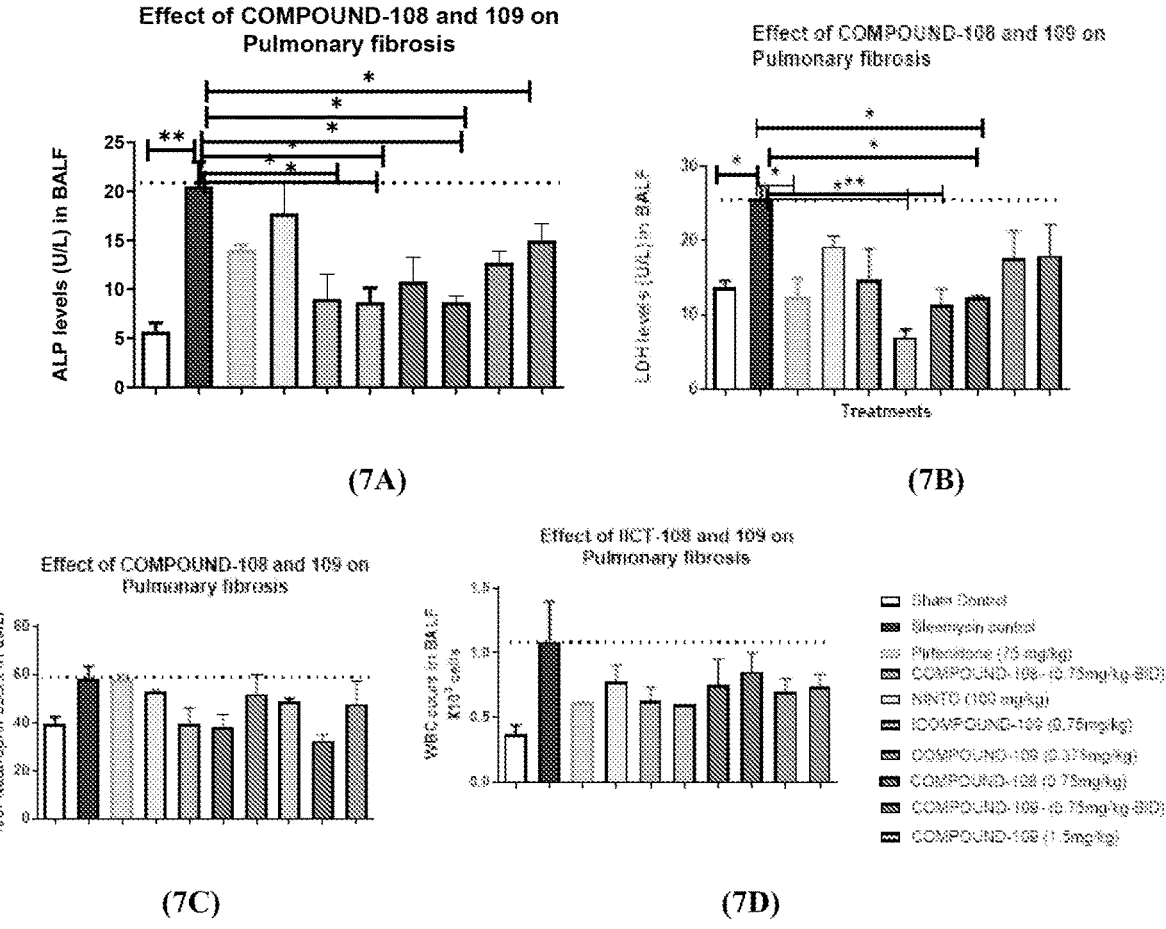
FIG. 7 depicts the effect of COMPOUND-108 and 109 against BLM induced inflammatory markers and neutrophils infiltration in Bronchiolar Lavage Fluid of the rats.
Figure 8:
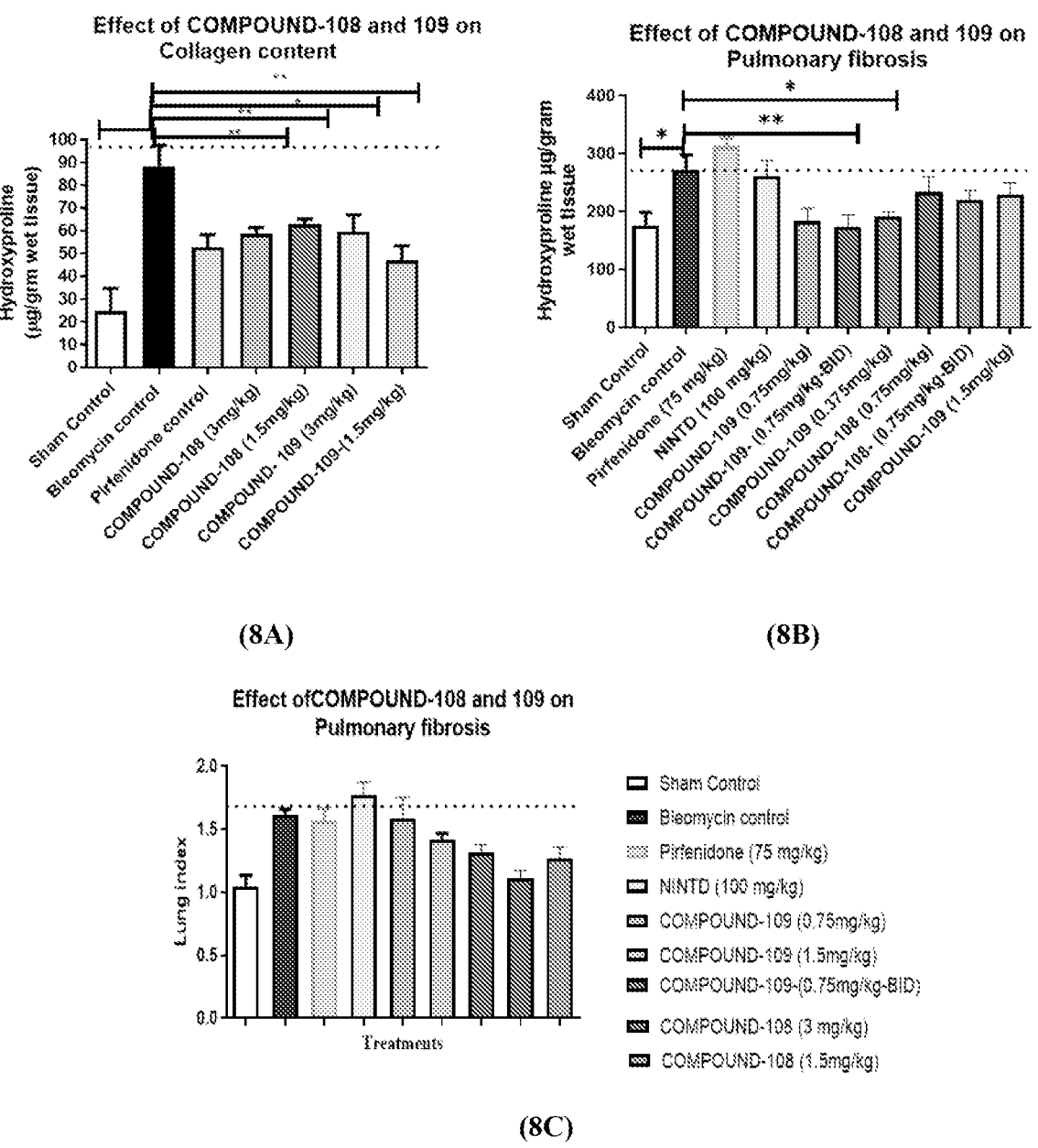
FIG. 8 depicts the effect of COMPOUND-108 and 109 against BLM increased collagen deposition and lung index.
Figure 9:
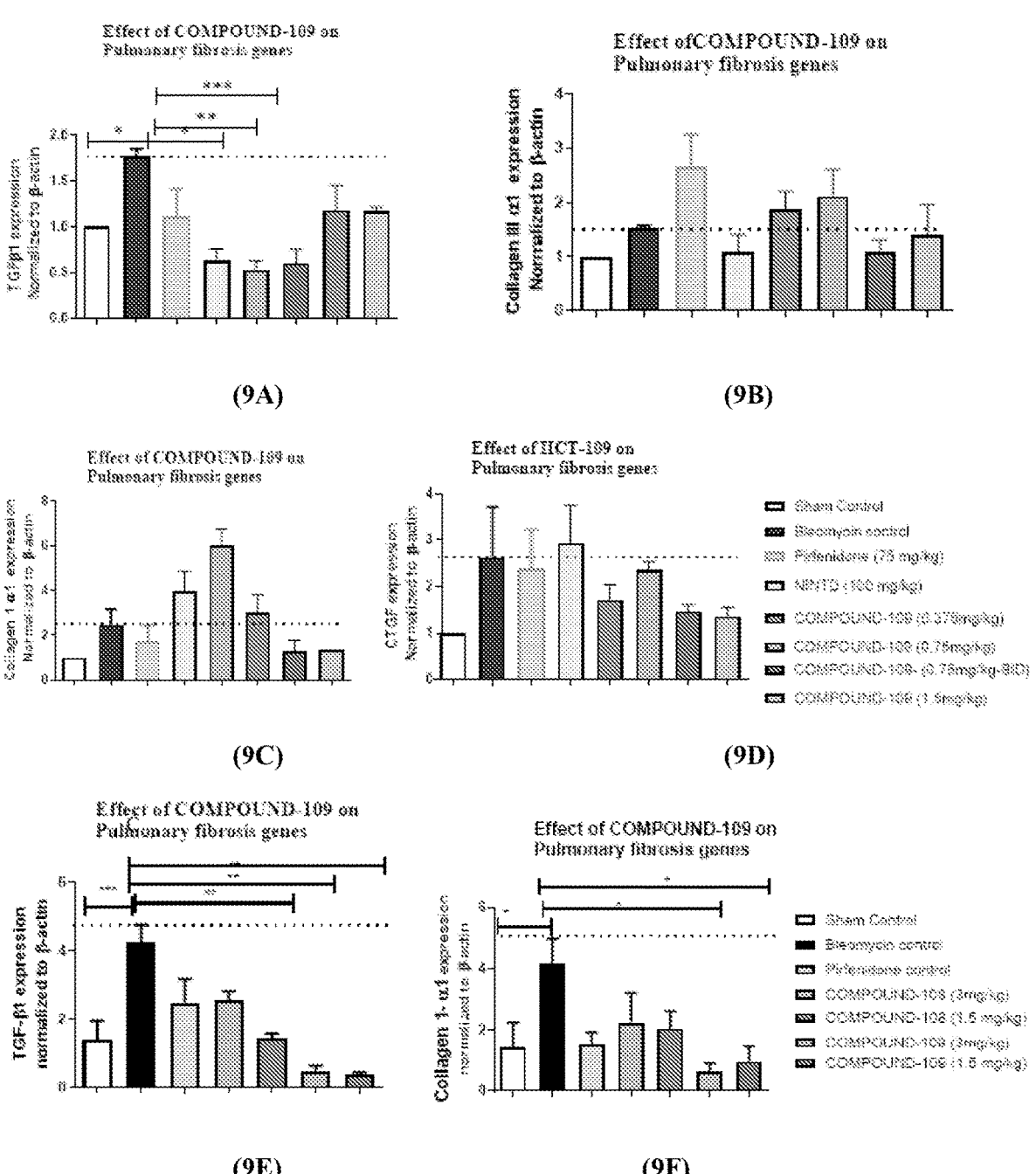
FIG. 9 depicts the effect of COMPOUND-108 and 109 against BLM increased levels of TGF-β, collagen 1α1, collagen 3α1 and CTGF mRNA levels in rat lung tissues.

EXAMPLE 6: HDAC-Inhibitors Attenuated BLM-Induced Pulmonary Fibrosis in Wistar Rats Bleomycin induced pulmonary fibrosis is a widely used in-vivo model to assess the antifibrotic activity against IPF. In this study, HDAC-inhibitors and standard drugs (as per Table 2 and 3) were administered orally for 14 days after intratracheal administration of Bleomycin as described in schematic plan (FIG. 6). Pro-Inflammatory markers such as ALP and LDH levels were significantly increased in BLM control samples, upon treatment with Compound-108 and 109, ALP and LDH levels were reduced in dose dependently (FIGS. 7A and 7B). Further, Neutrophil infiltration count and WBC count was measured in all the BALF samples, elevated levels of Neutrophil (FIG. 7C) and WBC (FIG. 7D) was observed in BLM disease group and those levels were reduced significantly with HDAC-inhibitors. BCA treatment markedly ameliorated the BLM induced increased collagen levels in the lungs (FIGS. 8A and 8BG) and lung index (FIG. 8C).

EXAMPLE 7: HDAC-Inhibitors Reduced the Collagen Marker's Expression by Modulating the TGF-β Levels in In-Vivo BLM treatment is known to increase the inflammation and growth factors in lung tissues, especially TGF-β1 induction upon BLM treatment lead to stimulate extra cellular matrix proteins and led to formation of collagen. HDAC-inhibitors treatments significantly attenuated the BLM induced TGF-β gene expression (FIGS. 9A and 9E) and other collagen markers expressions in dose dependent manner (FIGS. 9B, 9C, 9D and 9F).

Figure 10:
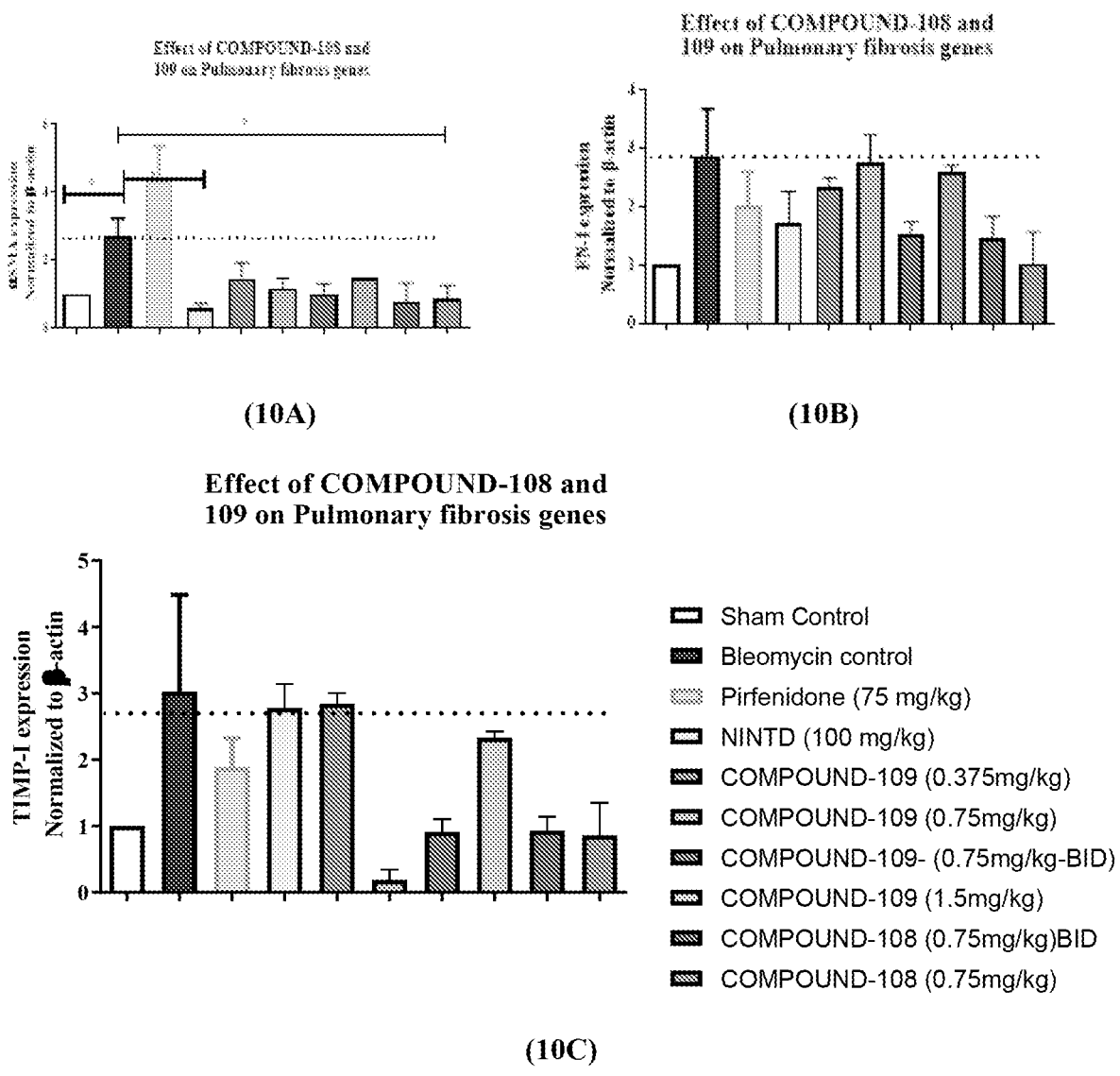
FIG. 10 depicts the effect of COMPOUND-108 and 109 against BLM increased levels of $\alpha$-SMA, Timp1 and Fibronectin1 (FN1) mRNA levels in rat lung tissues.

EXAMPLE 8: HDAC-Inhibitors Reduced the Fibrotic Marker's (EMT and ECM) Expression in BLM Induced Pulmonary Fibrosis Model Along with collagen levels, the effect of HDAC-inhibitors on EMT and ECM markers was tested. Treatment with HDAC inhibitors significantly attenuated the BLM induced α-SMA (FIG. 10A), FN1 (FIG. 10B) and TIMP1 (FIG. 10C) levels in rat tissues.

EXAMPLE 9: HDAC Inhibitors Protects Against Bleomycin-Induced Pathological Changes of Lungs Histopathological analysis by H&E (Fibrosis score) and Masson's staining (Ashcroft score) revealed that HDAC-inhibitors (COMPOUND-108 and 109) reduced the BLM induced thickened alveolar walls, few inflammatory cells infiltration, and reduced deposition of collagen fibers com-pared BLM alone group (FIGS. 11A, 11B, 11C and 12A, 12B, 12C). Collectively, in-vivo results delineated that, COMPOUND-108 and COMPOUND-109 could effectively protect the BLM-induced inflammation, fibrotic marker expression and pathological changes in lung tissues.
Results on ARDS Model:

EXAMPLE: 10

COMPOUND-108 Treatment Reduced the Infiltration of Neutrophils in BALF

Figure 13:
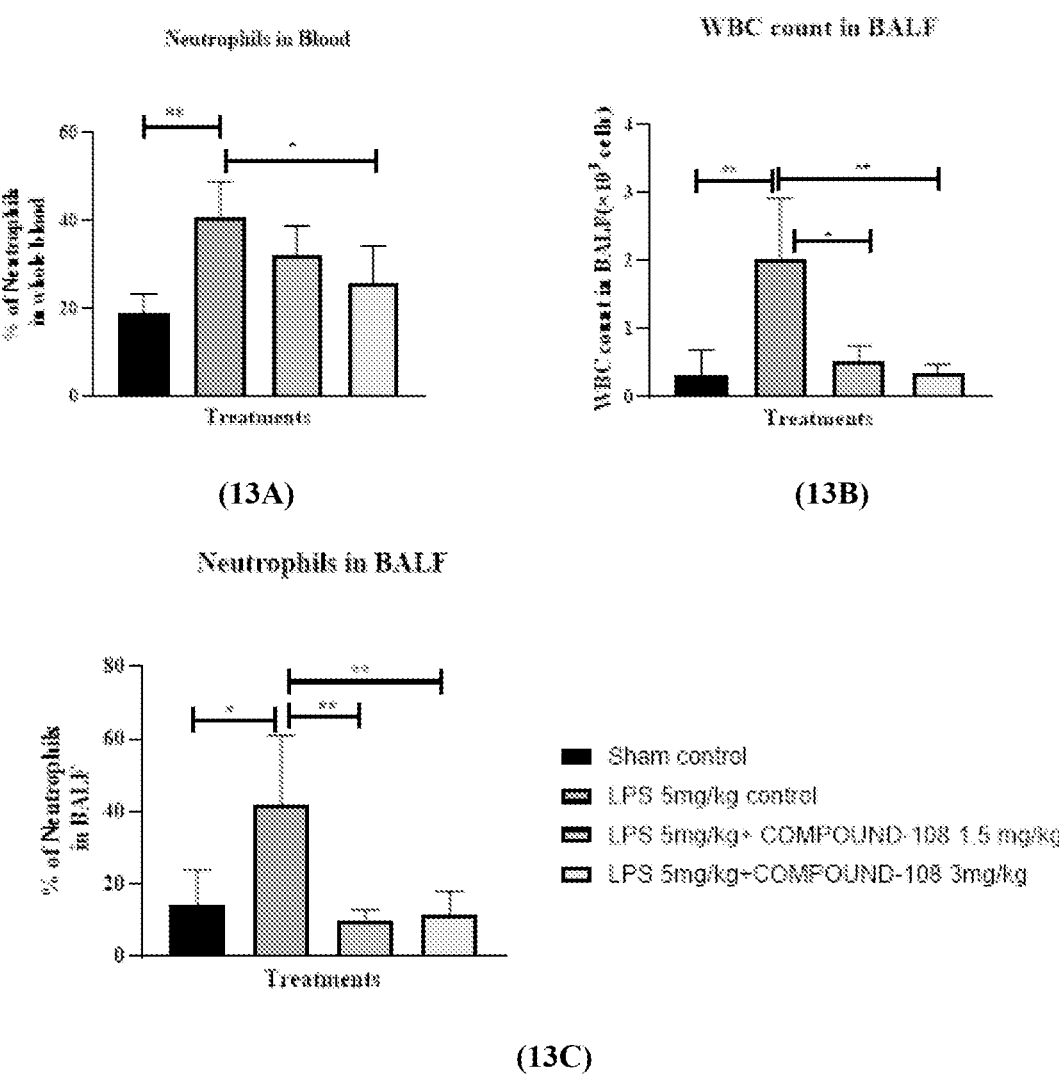
FIG. 13 depicts the effect of COMPOUND-108 against lipopolysaccharide (LPS) induced elevation of neutrophils in blood, WBC and neutrophils infiltration in Bronchiolar Lavage Fluid in rat lungs.

LPS induced significant increase in the Neutrophil count in blood in disease control group. COMPOUND-108 3 mg/kg treatment significantly attenuated the LPS induced Neutrophil count in blood (FIG. 13A). LPS induced signifi-cant increase in Neutrophil count and WBC count in Bron-choalveolar lavage fluid (BALF) in disease control. COM-POUND-108 treatment significantly attenuated the LPS induced infiltration of WBC (FIG. 13B) and Neutrophils (FIG. 13C).

EXAMPLE: 11

HDACi (COMPOUND-108) Reduced the Lung Oedema and Spleen Index

LPS induction significantly increased the Lung and spleen indices in disease control. COMPOUND-108 treatment sig-nificantly attenuated the LPS induced Lung volume (index) and spleen Indices (FIG. 14).

EXAMPLE: 12

Figure 15:
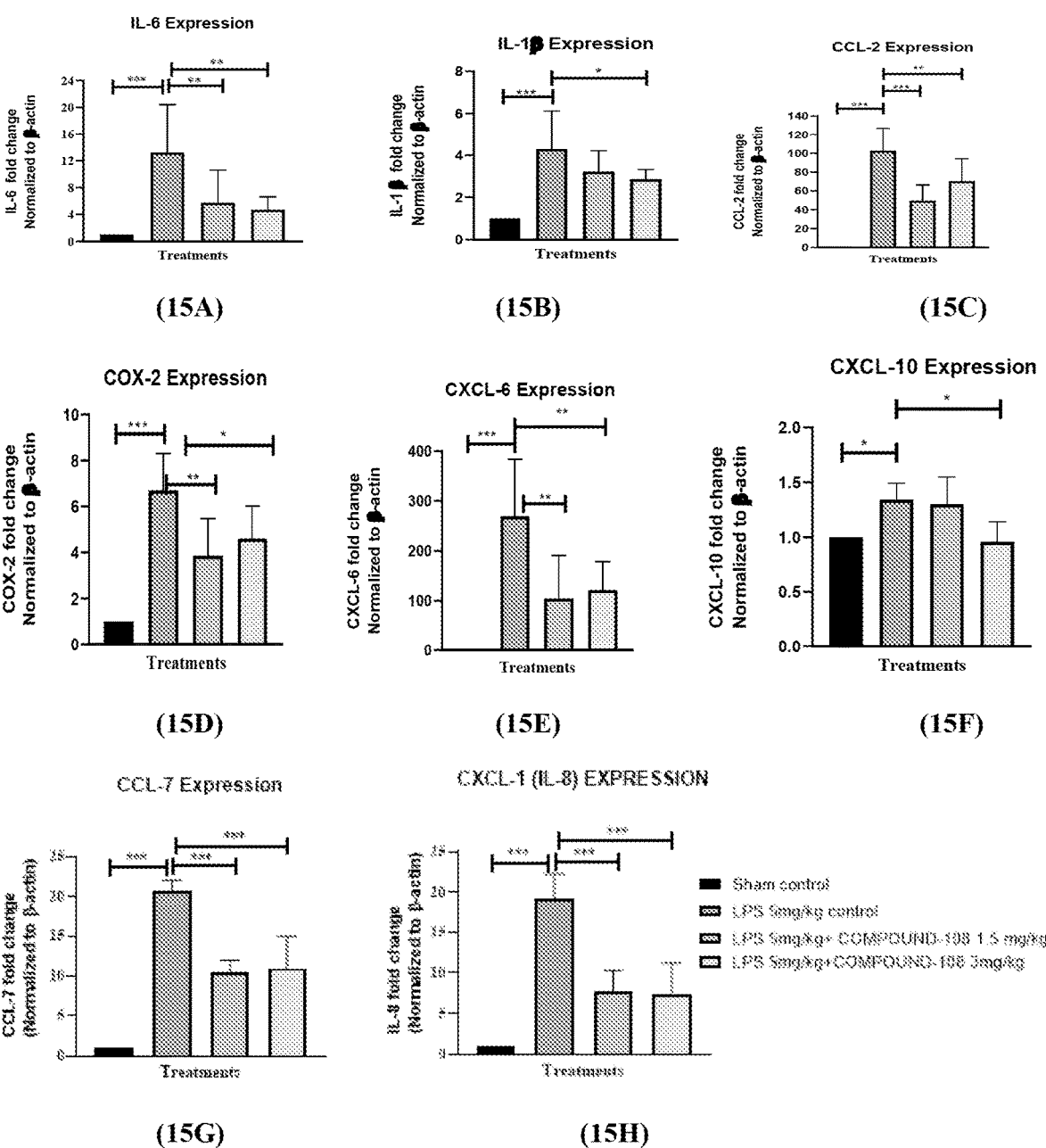
FIG. 15 depicts the effect of COMPOUND-108 against LPS increased levels of IL-6,IL-1beta, CCL-2, Cox-2, CXCL-6, CXCL-10, CCL-7 and CXCL-1 (IL-8 surrogate marker) mRNA levels in rat lung tissues

COMPOUND-108 Significantly Reduced the Expression of Pro-Inflammatory Cytokines and Chemokines Intratracheal (IT) administration of LPS significantly increased the expression of IL-6, IL-1β, CC12, Cox-2, CXCL-6, CCL-7, CXCL-1 (IL-8 surrogate marker) and CXCL-10 in the lung tissues of disease control animals. COMPOUND-108 treatment significantly attenuated the increased expression of LPS induced expression of inflammatory markers treated animals with dose dependent manner (FIG. 15).

EXAMPLE: 13

COMPOUND-108 Significantly Reduced the Expression of Chemokines and TLR3 Genes

Figure 16:
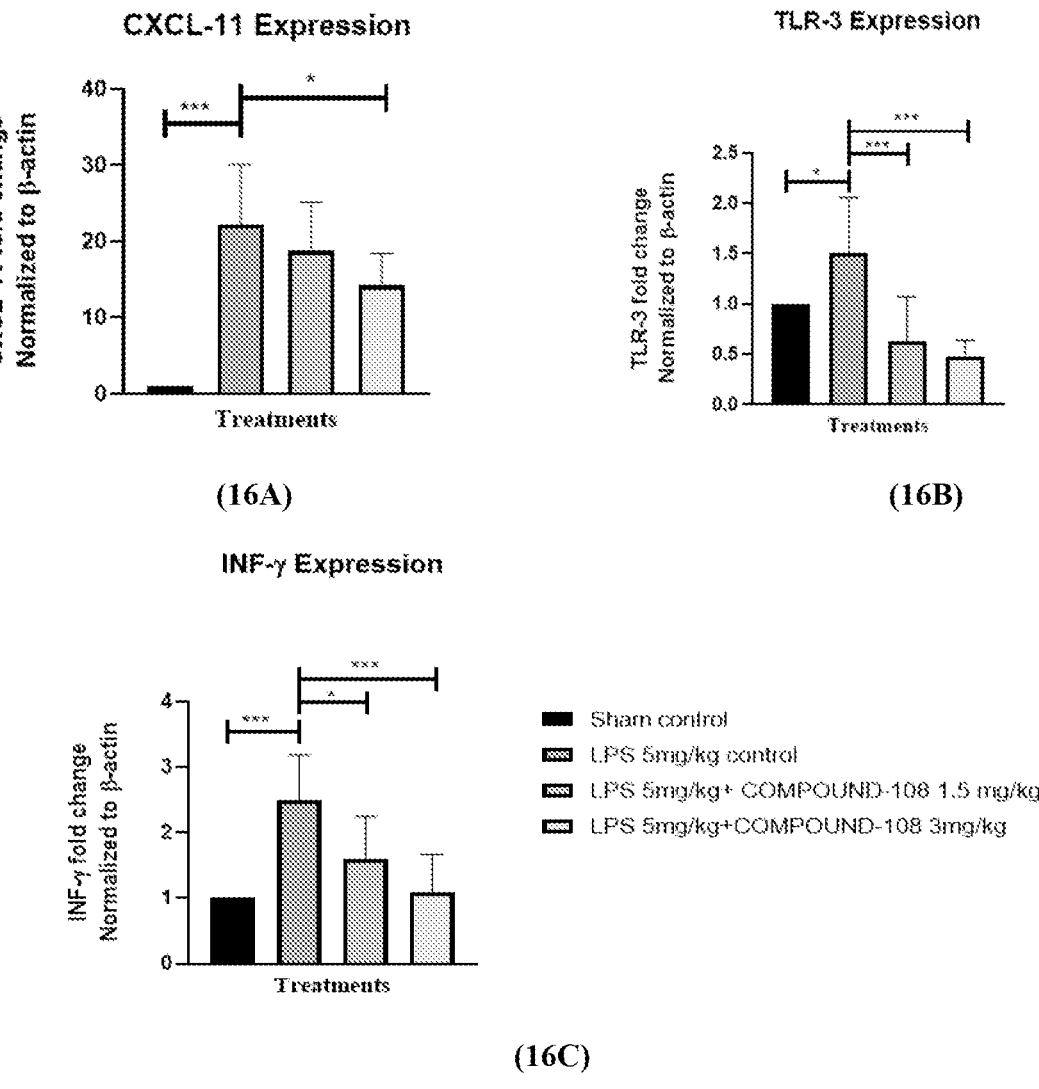
FIG. 16 depicts the effect of COMPOUND-108 against LPS increased levels of CXCL-11,TLR-3 and INF-$\gamma$ mRNA levels in rat lung tissues.

IT administration of LPS significantly increased the CXCL-11, TLR-3 and INF-γ expression in the lung tissues of disease control animals. COMPOUND-108 treatment significantly attenuated the LPS induced inflammatory marker's expression in dose dependent manner (FIG. 16).

EXAMPLE: 14

Treatment with COMPOUND-108 Attenuated the LPS Induced IL-6 Levels in Plasma Samples LPS challenge significantly increased the IL-6 levels in plasma. COMPOUND-108 (3 mg/kg) reduced the plasma IL-6 Levels at both the time points (FIG. 17).

EXAMPLE: 15

COMPOUND-108 Reverses Lung Injury and Pulmonary Edema in LPS Challenged Rats

Figure 18:
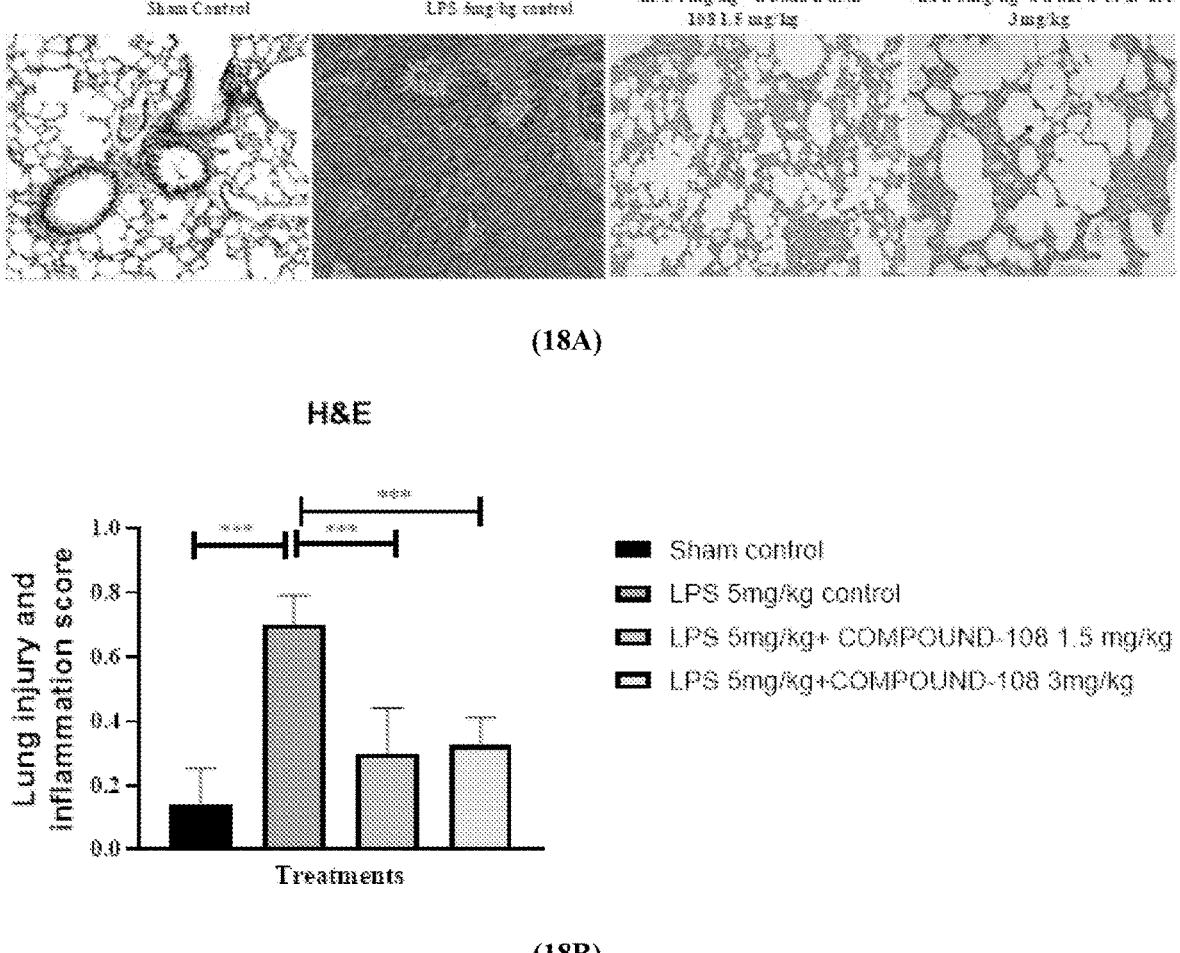
FIG. 18 depicts the effect of COMPOUND-108 against LPS induced inflammatory changes in lung tissues (H&E staining).

LPS instilled animal group exhibited severe pathological changes (Alveolar hemorrhages/congestion, alveolar/interstitial edema/degeneration, alveolar/interstitial infiltration of inflammatory cells specifically neutrophils, plasma cells, alveolar wall thickening alveolar/bronchiolar inflammation) and caused the endothelial barrier dysfunction. As evident from H&E results (FIG. 18), it was observed that inflammatory cells such as neutrophils influx into the alveolar spaces, thus led to the thickening of an interalveolar septum (FIG. 18A). Moreover, COMPOUND-108 pre-treatment remarkably repressed the pathological consequences (LPS induced) at 1.5 and 3 mg/kg doses. Overall, histopathological observation revealed that LPS+COMPOUND-1.5 mg/kg and LPS+COMPOUND-3 mg/kg group showed (18B) significant (p<0.01) reduction of lung injury and infiltration of inflammatory cells.

ADVANTAGES OF THE INVENTION

The present disclosure provides sulfonyl hydroxamine acid based HDACi compounds of formula 1 which are useful for preventing or treating ARDS.

The present disclosure also provides sulfonyl hydroxamine acid based HDACi compounds for use in preventing or treating IPF, ARDS and lung injury.

The present disclosure also provides a prophylactic or therapeutic agent for use in preventing or treating IPF and ARDS, which comprises the sulfonyl hydroxamine acid based HDACi compounds.

The sulfonyl hydroxamine acid compound of the present disclosure are useful in treating lung inflammatory disorders and fibrotic disorders, including Acute lung injury, Acute respiratory distress syndrome (ARDS), Idiopathic pulmonary fibrosis, hepatic fibrosis, cardiac fibrosis, and kidney fibrosis.

References:
1. George, P. M., Wells, A. U., Jenkins, R. G., Pulmonary fibrosis and COVID-19: the potential role for antifibrotic therapy. *The Lancet Respir. Med.* 2020 pages 807-815.

2. Spagnolo, P., Balestro, E., Aliberti, S., Cocconcelli, E., Biondini, D., Casa, G. D., Sverzellati, N., Maher, T. M., 2020. Pulmonary fibrosis secondary to COVID-19: a call to arms? *The Lancet Respir. Med* pages 750-752.

3. Wu C, Chen X, Cal Y, et al. Risk Factors Associated With Acute Respiratory Distress Syndrome and Death in Patients With Coronavirus Disease 2019 Pneumonia in Wuhan, China [published online ahead of print, 2020 Mar. 13]. *JAMA Intern Med.* 2020;180(7) pages 1-11. doi: 10.1001/jamainternmed.2020.0994

4. Uckun, F M, Hwang L, Trieu V, Selectively targeting TGF-β with Trabedersen/OT-101 in treatment of evolving and mild ARDS in COVID-19 *Clin. Invest.* (Lond.) (2020) 10(2), pages 167-17.

5. Richeldi L, Collard H R, Jones M G, Idiopathic pulmonary fibrosis, *The Lancet,* 389(10082)2017, Pages 1941-1952

6. P. J. Barnes, I. Adcock, Anti-inflammatory actions of steroids: molecular mechanisms *Trends Pharmacol Sci.,* 14 (1993), pages 436-441

7. Roy C. St. J, orinsky P M, Immunologic Therapy for ARDS, Septic Shock, and Multiple-Organ Failure, Clinical Implications of Basic Research 103(3), 1993, Pages 932-943

8. Khilnani, G C, Hadda, V,. "Corticosteroids and ARDS: A review of treatment and prevention evidence." *Lung India: official organ of Indian Chest Society,*28 (2) (2011): 114-9. doi:10.4103/0970-2113.80324

9. Tang, J, Yan, H, Zhuang, S, Histone deacetylases as targets for treatment of multiple diseases. *Clinical science* (London, England: 1979) 124 (11) (2013)pages 651-62. doi:10.1042/C520120504

10. Saito, S et al. Tubastatin ameliorates pulmonary fibrosis by targeting the TGFβ-PI3K-Akt pathway. *PloS one,* 12,10 e0186615.2017, doi:10.1371/journal.pone.0186615

11. Saito, S et al. HDAC8 inhibition ameliorates pulmonary fibrosis. *Am. J of Physiol. Lung cellular molecular physiology* 316(1) (2019): L175-L186. doi:10.1152/ajplung.00551.2017

12. Balaji, S A, Udupa N, Rao M C, Gupta V, Rangarajan A, Role of the Drug Transporter ABCC3 in Breast Cancer Chemoresistance. *PloS one,* 11(5) e0155013. doi:10.1371/journal.pone.0155013

13. Balaji S A, Karthik G, Krishna T S, Shaikh R B, Ramakrishna S, Biochanin-A ameliorates pulmonary fibrosis by suppressing the TGF-β mediated EMT, myofibroblasts differentiation and collagen deposition in in vitro and in vivo systems. *Phytomedicine,*78, 2020, 153298

14. Akgedik, R. Akgedik, S. Karamanli, H. Uysal, S. Bozkurt, B. Ozol, D. Armutcu, F. Yildiri mZ.Effect of Resveratrol on Treatment of Bleomycin-Induced Pulmonary Fibrosis in Rats, *Inflammation,* 35 (2012), pp. 1732-1741

15. Ashcroft T, Simpson J M, Timbrell V Simple method of estimating severity of pulmonary fibrosis on a numerical scale. *J Clin Pathol* 41: (1988) 467-470.

16. Zaghloul, M. S. Abdel-Salam, R. A. Said, E. Suddek, G. M. Salem H. A.-R Attenuation of Bleomycin-induced pulmonary fibrosis in rats by flavocoxid treatment *Egypt. J. Basic Appl. Sci.*4 (2017), pages 256-263

17. Korfei M, Stelmaszek D, MacKenzie B, Skwarna S, Chillappagari S, Bach A C, et al. (2018) Comparison of the antifibrotic effects of the pan-histone deacetylase-inhibitor panobinostat versus the IPF-drug pirfenidone in fibroblasts from patients with idiopathic pulmonary fibrosis. PLoS ONE 13(11): e0207915. https://doi.org/10.1371/journal-.pone.0207915

18. Shu, D. Y., & Lovicu, F. J. (2017). Myofibroblast transdifferentiation: The dark force in ocular wound healing and fibrosis. *Progress in retinal and eye research,* 60, 44-65. https://doi.org/10.1016/j.preteyeres.2017.08.001

We claim:

1. A method of treating a condition selected from lung inflammatory disorders, and fibrotic disorders, wherein the method comprises administering to a patient in need of such treatment a therapeutically effective amount of sulfonyl hydroxamine acid compound of formula 1

Formula 1 wherein

Ring A and B are independently selected from aryl, heteroaryl, cycloalkyl, fused aryl, or fused alkyl group;

$R_1$, $R_2$, $R_3$, $R_4$, $R_5$, $R_6$ and $R_7$ are independently selected from hydrogen, alkoxy, aryloxy, hydroxy, ester, amide, amino, alkyl, aryl, heteroaryl, halogen, nitro, cyano, and aldehyde; and X is O; and wherein the sulfonyl hydroxamine acid compound of formula 1 selectively inhibit HDAC-6 and/or HDAC-8.

2. The method of claim 1, wherein the compound is:

107

108

22

-continued

109

110

3. The method of claim 1, wherein the lung inflammatory disorders related to cytokine storm comprise Acute lung injury, Acute respiratory distress syndrome (ARDS), or Idiopathic pulmonary fibrosis, or wherein the fibrotic disorders comprise hepatic fibrosis, cardiac fibrosis, or kidney fibrosis.

4. The method of claim 1, further comprising attenuating the lipopolysaccharides (LPS) induced infiltration of WBC and Neutrophils.

5. The method of claim 1, further comprising attenuating the LPS induced Lung volume (index), and spleen Indices.

6. The method of claim 1, further comprising reducing the expression of inflammatory markers consisting of pro-inflammatory cytokines (IL-6, IL-1β or IL-8), chemokines (CCL2 or CCL-7) or chemokine ligands (CXCL-6, CXCL-10 or CXCL-11), and TLR3 genes.

7. The method of claim 1, further comprising attenuating the LPS induced IL-6 levels in plasma samples.

8. The method of claim 1, further comprising attenuating the extra cellular matrix proteins, collagen, and epithelial to mesenchymal markers expression in TGF-β stimulated LL29, DHLF, or NHLF cells.

9. The method of claim 1, further comprising mitigating the inflammatory markers expression and infiltration of neutrophils in BLM challenged rats.

10. The method of claim 1, further comprising reducing the lung index and hydroxyproline levels in BLM challenged rats.

11. The method of claim 1, further comprising attenuating the fibrotic markers expression in BLM challenged rats.

12. The method of claim 1, wherein the effective dose ranges between 2 mg/kg to 4 mg/kg body weight.

* * * * *